(12) United States Patent
Lee et al.

(10) Patent No.: US 9,486,133 B2
(45) Date of Patent: Nov. 8, 2016

(54) SURGICAL ACCESS SYSTEM AND RELATED METHODS

(75) Inventors: James Coleman Lee, San Diego, CA (US); Benjamin VerHage, New York, NY (US); Michael Serra, San Diego, CA (US); Troy D. Woolley, Erie, CO (US); Brian Snider, San Diego, CA (US); Matthew Schwartz, San Diego, CA (US)

(73) Assignee: NUVASIVE, INC., San Diego, CA (US)

( * ) Notice: Subject to any disclaimer, the term of this patent is extended or adjusted under 35 U.S.C. 154(b) by 698 days.

(21) Appl. No.: 13/821,224
(22) PCT Filed: Aug. 23, 2011
(86) PCT No.: PCT/US2011/001489
§ 371 (c)(1),
(2), (4) Date: Jan. 27, 2014
(87) PCT Pub. No.: WO2012/026981
PCT Pub. Date: Mar. 1, 2012

(65) Prior Publication Data
US 2014/0135584 A1 May 15, 2014

Related U.S. Application Data

(60) Provisional application No. 61/376,163, filed on Aug. 23, 2010, provisional application No. 61/390,248, filed on Oct. 6, 2010, provisional application No. 61/473,138, filed on Apr. 7, 2011.

(51) Int. Cl.
*A61B 1/32* (2006.01)
*A61B 17/02* (2006.01)
(Continued)

(52) U.S. Cl.
CPC ............ *A61B 1/32* (2013.01); *A61B 5/04001* (2013.01); *A61B 5/4836* (2013.01); *A61B 17/02* (2013.01);
(Continued)

(58) Field of Classification Search
CPC .... A61B 1/32; A61B 17/02; A61B 17/0206; A61B 17/0256; A61B 17/0262; A61B 2017/0262
See application file for complete search history.

(56) References Cited

U.S. PATENT DOCUMENTS

| 1,194,319 A | 8/1916 | Pretts |
| 2,693,795 A | 11/1954 | Grieshaber |

(Continued)

FOREIGN PATENT DOCUMENTS

| CA | 1142826 | 3/1983 |
| CN | 203506775 | 4/2014 |

(Continued)

OTHER PUBLICATIONS

International Search Report in the corresponding International Application No. PCT/US2011/001489, mailed Dec. 13, 2011 (3 pages).

(Continued)

*Primary Examiner* — Larry E Waggle, Jr.
(74) *Attorney, Agent, or Firm* — Rory Schermerhorn

(57) ABSTRACT

A surgical access system comprising a tissue dilation assembly and a tissue retraction assembly, both of which may be equipped with one or more electrodes for use in detecting the existence of (and optionally the distance and/or direction to) neural structures. A retractor assembly for creating an operative corridor to a spinal surgical target site is disclosed, comprising: a retractor body and a plurality retractor blades extending generally perpendicularly to the retractor body, the retractor body being operable to separate the at plurality of retractor blades relative to each; and a supplemental retractor blade assembly attachable to at least two of the plurality of retractor blades, the supplemental retractor blade assembly comprising an elongated supplemental retractor blade and a crossbar connector, the crossbar connector configured to be attached to said at least two retractor blades while engaging the supplemental retractor blade.

20 Claims, 33 Drawing Sheets

(51) Int. Cl.
  *A61N 1/05* (2006.01)
  *A61N 1/36* (2006.01)
  *A61N 1/372* (2006.01)
  *A61B 5/04* (2006.01)
  *A61B 5/0488* (2006.01)
  *A61B 17/00* (2006.01)
  *A61B 5/00* (2006.01)

(52) U.S. Cl.
  CPC ......... *A61B 17/0206* (2013.01); *A61N 1/0551* (2013.01); *A61N 1/36017* (2013.01); *A61N 1/36135* (2013.01); *A61N 1/37241* (2013.01); *A61N 1/37247* (2013.01); *A61B 5/0488* (2013.01); *A61B 5/4893* (2013.01); *A61B 5/6886* (2013.01); *A61B 90/30* (2016.02); *A61B 2017/00039* (2013.01); *A61B 2017/0046* (2013.01); *A61B 2017/00407* (2013.01); *A61B 2017/00477* (2013.01); *A61B 2017/00725* (2013.01); *A61B 2017/0256* (2013.01); *A61B 2017/0262* (2013.01)

(56) References Cited

U.S. PATENT DOCUMENTS

| | | |
|---|---|---|
| 2,807,259 A | 9/1957 | Guerriero |
| 3,467,079 A | 9/1969 | James |
| 3,509,873 A | 5/1970 | Karlin |
| 3,680,546 A | 8/1972 | Asrican |
| 3,724,449 A | 4/1973 | Gauthier |
| 3,740,839 A | 6/1973 | Otte |
| 3,888,117 A | 6/1975 | Lewis |
| 3,998,217 A | 12/1976 | Trumbull |
| 4,010,741 A | 3/1977 | Gauthier |
| 4,156,424 A | 5/1979 | Burgin |
| 4,165,746 A | 8/1979 | Burgin |
| 4,617,916 A | 10/1986 | Levahn |
| 4,627,421 A | 12/1986 | Symbas |
| 4,726,356 A | 2/1988 | Santilli |
| 4,813,401 A | 3/1989 | Grieshaber |
| 4,945,896 A * | 8/1990 | Gade ............... A61B 5/0084 600/202 |
| 4,955,884 A | 9/1990 | Grossi |
| 5,052,374 A | 10/1991 | Alvarez-Jacinto |
| 5,152,279 A | 10/1992 | Wilk |
| 5,195,505 A | 3/1993 | Josefsen |
| 5,199,419 A | 4/1993 | Remiszewski |
| 5,231,974 A | 8/1993 | Giglio |
| 5,280,782 A | 1/1994 | Wilk |
| 5,339,801 A | 8/1994 | Poloyko |
| 5,375,481 A | 12/1994 | Cabrera |
| 5,474,056 A | 12/1995 | Laborie |
| 5,520,610 A | 5/1996 | Giglio |
| 5,772,583 A | 6/1998 | Wright |
| 5,785,647 A | 7/1998 | Tompkins |
| 5,807,270 A | 9/1998 | Williams |
| 5,885,210 A | 3/1999 | Cox |
| 5,902,233 A | 5/1999 | Farley |
| 5,944,658 A | 8/1999 | Koros |
| 5,947,896 A | 9/1999 | Sherts |
| 6,024,696 A | 2/2000 | Hoftman |
| 6,050,996 A | 4/2000 | Schmaltz |
| 6,074,343 A | 6/2000 | Nathanson |
| 6,083,154 A | 7/2000 | Liu |
| 6,099,468 A | 8/2000 | Santilli |
| 6,213,940 B1 | 4/2001 | Sherts |
| 6,224,545 B1 | 5/2001 | Cocchia |
| 6,231,506 B1 | 5/2001 | Hu |
| 6,254,532 B1 | 7/2001 | Paolitto |
| 6,264,605 B1 | 7/2001 | Scirica |
| 6,273,853 B1 | 8/2001 | Cartier |
| 6,283,912 B1 | 9/2001 | Hu |
| 6,322,500 B1 | 11/2001 | Sikora |
| 6,340,345 B1 | 1/2002 | Lees |
| 6,511,423 B2 | 1/2003 | Farley |
| 6,685,632 B1 | 2/2004 | Hu |
| 6,712,795 B1 | 3/2004 | Cohen |
| 6,837,851 B1 | 1/2005 | Valentini |
| 6,849,064 B2 | 2/2005 | Hamada |
| 6,929,606 B2 | 8/2005 | Ritland |
| 6,945,933 B2 | 9/2005 | Branch |
| 6,951,538 B2 | 10/2005 | Ritland |
| 6,994,669 B1 | 2/2006 | Gannoe |
| 7,052,457 B2 | 5/2006 | Fanous |
| 7,135,020 B2 | 11/2006 | Lawes |
| 7,141,015 B2 | 11/2006 | Ruane |
| 7,160,298 B2 | 1/2007 | Lawes |
| 7,182,729 B2 | 2/2007 | Abdelgany |
| 7,374,534 B2 | 5/2008 | Dalton |
| 7,435,219 B2 | 10/2008 | Kim |
| 7,481,766 B2 | 1/2009 | Lee |
| 7,537,565 B2 | 5/2009 | Bass |
| 7,582,058 B1 | 9/2009 | Miles |
| 7,632,269 B2 | 12/2009 | Truckai |
| 7,641,659 B2 | 1/2010 | Emstad |
| 7,691,057 B2 | 4/2010 | Miles |
| 7,819,801 B2 | 10/2010 | Miles |
| 7,850,608 B2 | 12/2010 | Hamada |
| 7,905,840 B2 | 3/2011 | Pimenta |
| 7,922,657 B2 | 4/2011 | Gillinov |
| 7,931,589 B2 | 4/2011 | Cohen |
| 7,931,591 B2 | 4/2011 | McCarthy |
| 7,946,982 B2 | 5/2011 | Hamada |
| 7,976,463 B2 | 7/2011 | Dewey |
| 7,981,031 B2 | 7/2011 | Frasier |
| 8,100,828 B2 | 1/2012 | Frey |
| 8,137,284 B2 | 3/2012 | Miles |
| 8,152,714 B2 | 4/2012 | Garcia-Bengochea |
| 8,152,720 B2 | 4/2012 | Loftus |
| 8,206,293 B2 | 6/2012 | Reglos |
| 8,226,554 B2 | 7/2012 | McBride |
| 8,251,997 B2 | 8/2012 | Michelson |
| 8,257,255 B2 | 9/2012 | Farley |
| 8,262,570 B2 | 9/2012 | White |
| 8,267,859 B2 | 9/2012 | Holmes |
| 8,313,430 B1 | 11/2012 | Pimenta |
| 8,360,971 B2 | 1/2013 | Farley |
| 8,425,602 B2 | 4/2013 | Guyer |
| 8,449,463 B2 | 5/2013 | Nunley |
| 8,517,935 B2 | 8/2013 | Marchek |
| 8,562,621 B2 | 10/2013 | Mignucci |
| 8,568,306 B2 | 10/2013 | Hardenbrook |
| 8,636,655 B1 | 1/2014 | Childs |
| 8,636,656 B2 | 1/2014 | Nichter |
| 8,715,175 B2 | 5/2014 | Assaker |
| 8,821,394 B2 | 9/2014 | Hawkins |
| 8,821,396 B1 | 9/2014 | Miles |
| 8,852,090 B2 | 10/2014 | Friedrich |
| 8,876,687 B2 | 11/2014 | Jones |
| 8,882,661 B2 | 11/2014 | Hutton |
| 2004/0133077 A1* | 7/2004 | Obenchain ......... A61B 17/0206 600/224 |
| 2004/0181165 A1* | 9/2004 | Hoey .................. A61B 5/0537 600/547 |
| 2006/0074278 A1 | 4/2006 | Petit |
| 2006/0224044 A1 | 10/2006 | Marchek |
| 2007/0038033 A1 | 2/2007 | Jones |
| 2007/0156025 A1 | 7/2007 | Marchek |
| 2007/0208228 A1 | 9/2007 | Pavento |
| 2007/0282171 A1* | 12/2007 | Karpowicz .............. A61B 1/32 600/224 |
| 2007/0290369 A1 | 12/2007 | Hasegawa |
| 2008/0183044 A1 | 7/2008 | Colleran |
| 2008/0183214 A1 | 7/2008 | Copp |
| 2008/0234550 A1 | 9/2008 | Hawkes |
| 2009/0018399 A1 | 1/2009 | Martinelli |
| 2009/0062619 A1 | 3/2009 | Bjork |
| 2009/0069635 A1 | 3/2009 | Gephart |
| 2009/0076516 A1 | 3/2009 | Lowry |
| 2009/0105547 A1 | 4/2009 | Vayser |
| 2009/0156902 A1* | 6/2009 | Dewey ............... A61B 17/0206 600/204 |

(56) References Cited

U.S. PATENT DOCUMENTS

| | | | |
|---|---|---|---|
| 2009/0221878 A1* | 9/2009 | Gorek | A61B 17/0218 |
| | | | 600/206 |
| 2009/0264710 A1 | 10/2009 | Chana | |
| 2010/0160738 A1* | 6/2010 | Miles | A61B 1/32 |
| | | | 600/202 |
| 2010/0312068 A1 | 12/2010 | Dalton | |
| 2011/0137130 A1 | 6/2011 | Thalgott | |
| 2011/0144450 A1 | 6/2011 | Paolitto | |
| 2011/0172494 A1 | 7/2011 | Bass | |
| 2011/0224497 A1 | 9/2011 | Weiman | |
| 2011/0237902 A1 | 9/2011 | Rosen | |
| 2011/0301421 A1 | 12/2011 | Michaeli | |
| 2011/0301422 A1 | 12/2011 | Woolley | |
| 2011/0301423 A1 | 12/2011 | Koros | |
| 2012/0046527 A1 | 2/2012 | Cianfrani | |
| 2012/0083662 A1 | 4/2012 | Hamada | |
| 2012/0130180 A1 | 5/2012 | Pell | |
| 2012/0136392 A1 | 5/2012 | Keegan | |
| 2012/0203070 A1 | 8/2012 | Crenshaw | |
| 2012/0245431 A1 | 9/2012 | Baudouin | |
| 2012/0245432 A1 | 9/2012 | Karpowicz | |
| 2012/0330106 A1 | 12/2012 | Wright | |
| 2013/0123581 A1 | 5/2013 | Fritzinger | |
| 2013/0158359 A1 | 6/2013 | Predick | |
| 2013/0190575 A1 | 7/2013 | Mast | |
| 2013/0261401 A1 | 10/2013 | Hawkins | |
| 2014/0024900 A1 | 1/2014 | Capote | |
| 2014/0066718 A1 | 3/2014 | Fiechter | |
| 2014/0073857 A1 | 3/2014 | Dodson | |
| 2014/0128979 A1 | 5/2014 | Womble | |

FOREIGN PATENT DOCUMENTS

| | | |
|---|---|---|
| DE | 4425652 | 2/1996 |
| EP | 0951868 | 10/1999 |
| EP | 1829488 | 9/2007 |
| JP | 3187929 | 12/2013 |
| WO | WO-9320741 | 10/1993 |
| WO | WO-03017847 | 3/2003 |
| WO | WO-2005016131 | 2/2005 |
| WO | WO-2007002405 | 1/2007 |
| WO | WO-2010121291 | 10/2010 |
| WO | WO-2010125598 | 11/2010 |
| WO | WO-2010136860 | 12/2010 |
| WO | WO-2012093368 | 7/2012 |
| WO | WO-2013000105 | 1/2013 |

OTHER PUBLICATIONS

Written Opinion of the International Searching Authority in the corresponding International Application No. PCT/US2011/001489, mailed Dec. 13, 2011 (7 pages).

* cited by examiner

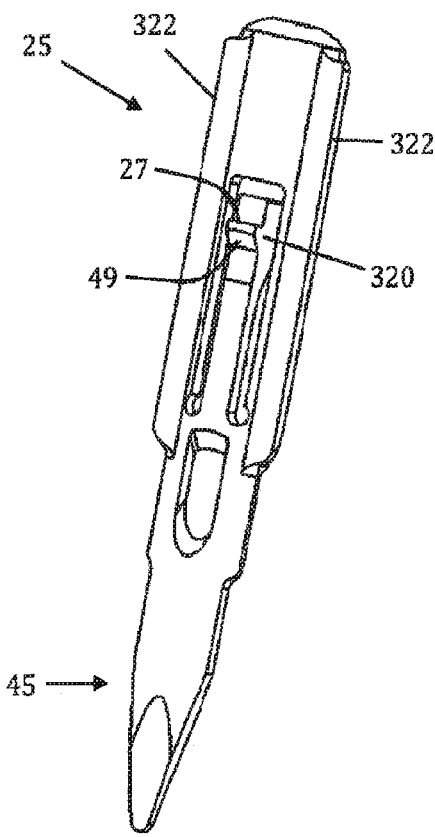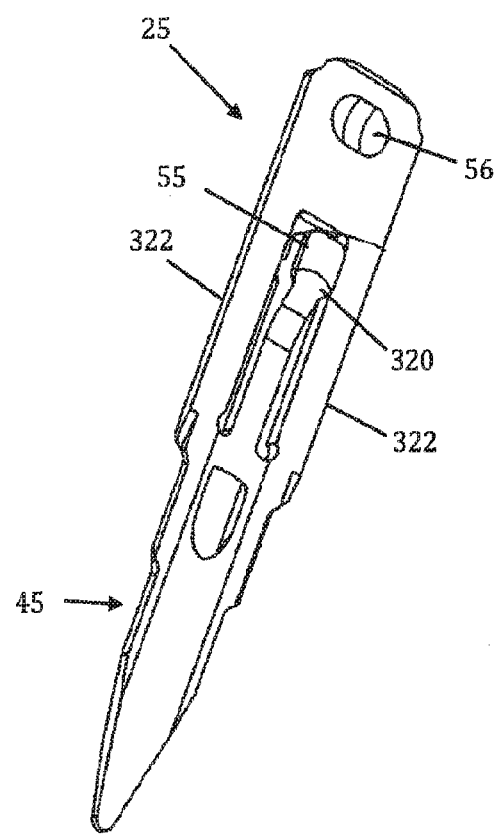
Fig. 11　　　　　Fig. 12
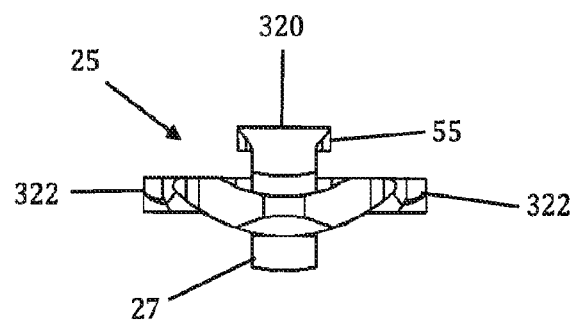
Fig. 13

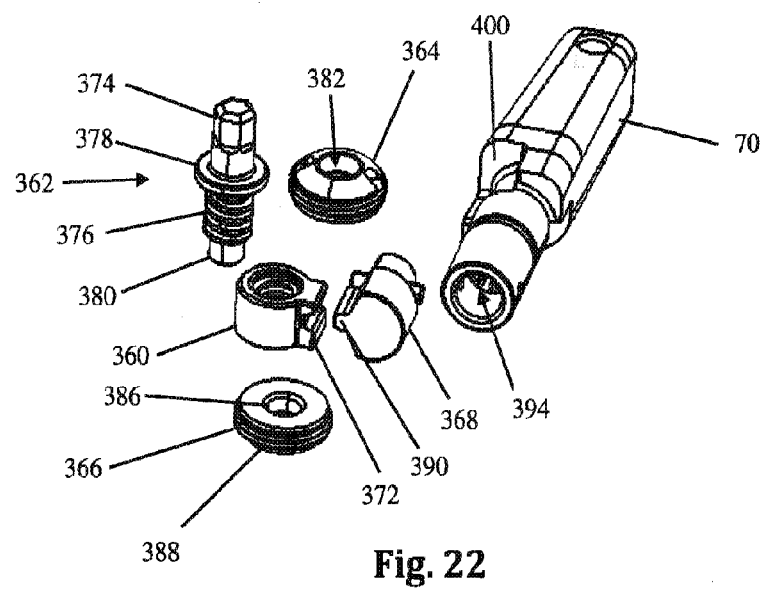
Fig. 22
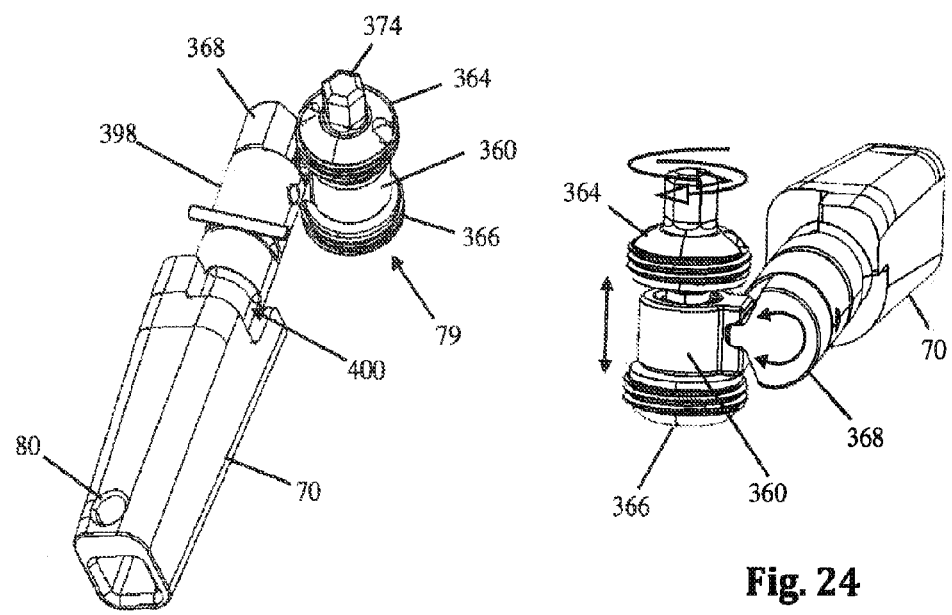
Fig. 23
Fig. 24

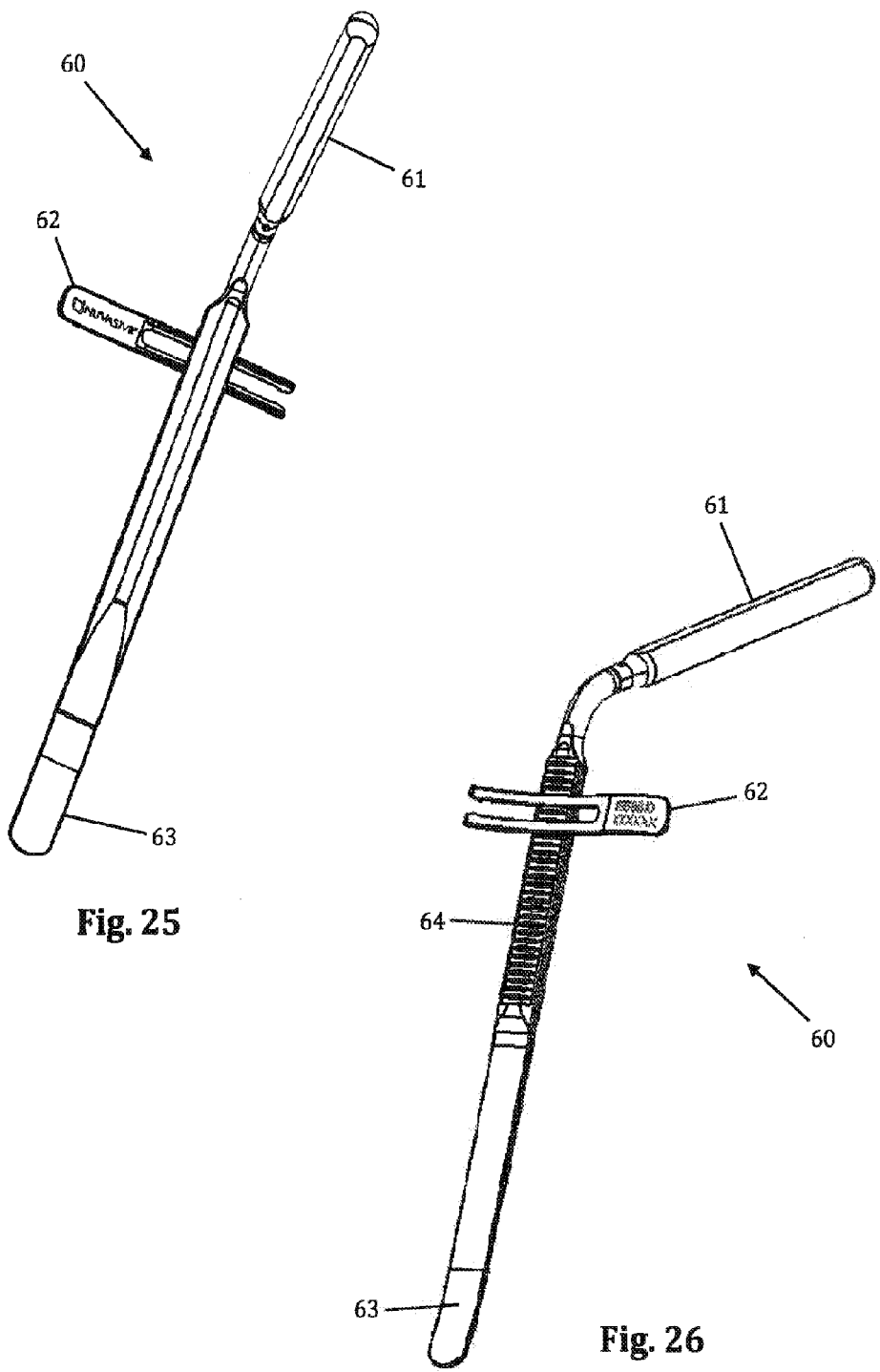

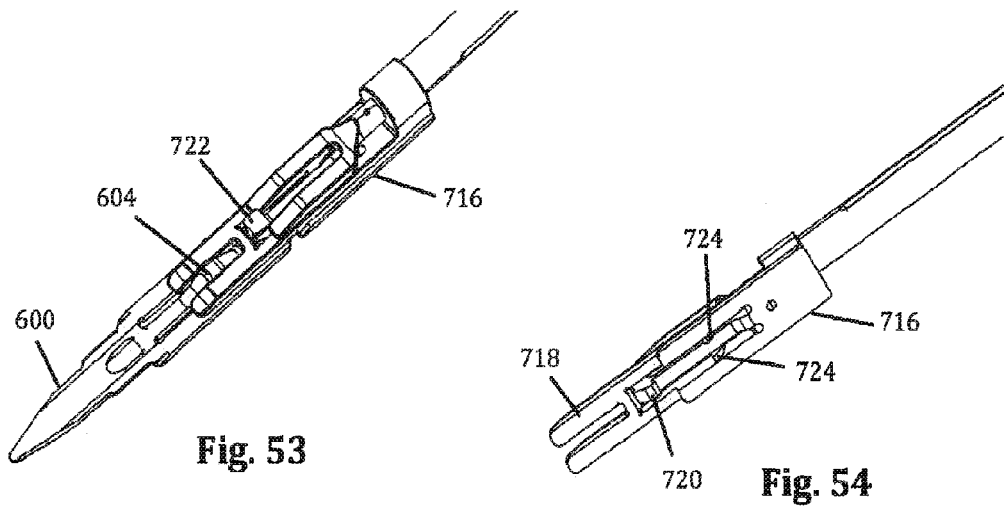
Fig. 53
Fig. 54
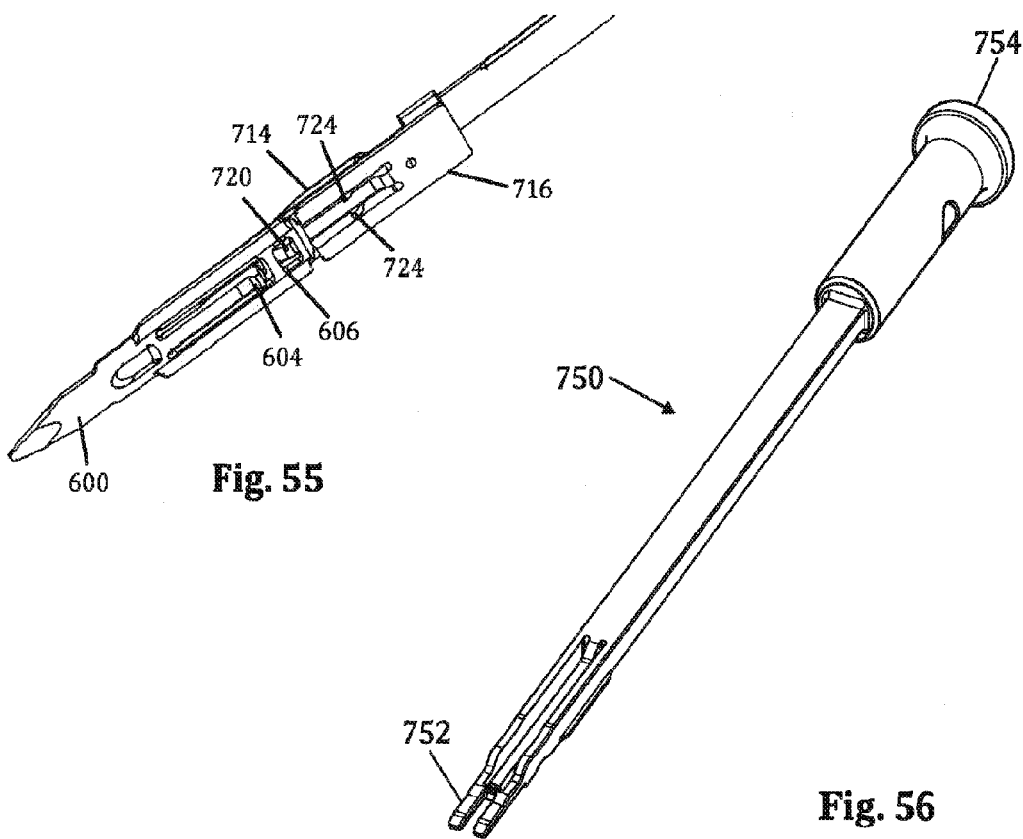
Fig. 55
Fig. 56

SURGICAL ACCESS SYSTEM AND RELATED METHODS

CROSS-REFERENCES TO RELATED APPLICATIONS

This international (PCT) patent application claims priority to U.S. Provisional Application Ser. No. 61/376,163 filed Aug. 23, 2010, U.S. Provisional Application Ser. No. 61/390,248 filed Oct. 6, 2010, and U.S. Provisional Application Ser. No. 61/473,138 filed Apr. 22, 2011, the complete disclosures of each of which are hereby incorporated by reference into this application as if set forth fully herein.

FIELD

This disclosure relates to a surgical retraction system and related instrumentation and methods for accessing a surgical target site for the purpose of performing surgical procedures.

BACKGROUND

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. On such minimally invasive approach, a lateral trans-psoas approach to the spine, developed by NuVasive®, Inc., San Diego, Calif. (XLIF®) has demonstrated great success in reducing patient morbidity, shortening the length of hospitalization and fast recovery time when it is employed. Improvement of instruments and methods employed to the during the lateral access has the potential to further reduce operative time, expand applications for the lateral approach, and increase surgeon adoption of the procedure, all of which will ultimately benefit the patient by provide more opportunity for minimally invasive surgical correction of their ailments. The instruments and methods described herein are designed to address these needs, among others.

SUMMARY

The present application describes systems and methods for performing surgical procedures on the spine, including (according to a preferred method) creating an operative corridor to the spine via a substantially lateral, trans-psoas approach. The access described herein is accomplished with a surgical access system including a dilation assembly and a retraction assembly. To create the lateral access corridor to the lumbar spine, the patient is positioned on their side and the surgical access system is advanced through an incision, into the retroperitoneal space, and then through the psoas muscle until the targeted spinal site (e.g. the disc space between a pair of adjacent vertebral bodies) is reached. The access system may include a sequential dilation system of increasing diameter and a tissue retractor assembly. The sequential dilation assembly is advanced to the target site first and the retractor assembly is then advanced to the target site over the sequential dilation system. Nerve monitoring may be performed while advancing each of the dilation system and retraction system to the target site to detect the presence of, and thereby avoid, nerves lying in the trans-psoas path to the target site.

The retractor assembly includes a plurality of retractor blades, three according to a preferred embodiment, and a body. The retractor assembly is then operated to expand the operative corridor to the desired geometry and dimension. The body includes two arms connected to each other by a pivot. Handle extenders may be attached to the arms and squeezed to cause the cephalad-most and caudal most arms to move away from each other and away from the posterior blade (which may preferably be fixed in position) to expand the operative corridor anteriorly (away from the nerves posterior to the posterior blade). The cephalad-most and caudal-most blades may also pivot or splay outward from a central axis of insertion to expand the operative corridor at the surgical site without increasing the size of the incision. The retractor assembly exhibits continuous splay such that splay to any angle (within a predetermined range) may be achieved. The continuous splay is achieved through the use of a gear mechanism coupled to each arm of the retractor body. The gear mechanism may be a lead screw driven rack and pinion gear. The rack may translate vertically in the retractor body causing the pinion to rotate. The pinion is connected to one end of a rotating arm which is coupled at the opposite end to one of the retractor blades to be splayed. Each of the two gear mechanisms (one for each arm of the retractor) operates independently such that the blades can be adjusted independent of each other.

According to one example, the posterior most of the blades may be fixed in position relative to the spine prior to operating the retractor to open the blades. This may be accomplished, for example, by attaching an interdiscal shim to the blade and inserting the distal end of the shim into the disc space. Alternatively, or in addition, this may be accomplished by connecting an articulating arm between the surgical table (or other suitable mount) and posterior blade (via a translating arm to which the posterior blade is attached). In this manner, the posterior blade will not move posteriorly towards nerve tissue located in the posterior portion of the psoas muscle. Instead, the remaining blades and will move away from the posterior blade to expand the access corridor. In addition to the interdiscal shim, blade extenders may be coupled to the cephalad and caudal blades. The extenders may have contoured distal ends to match the anatomy at the anterior of the vertebral body.

The retractor assembly may be configured to employ a supplemental anterior retractor blade. The supplemental anterior retractor blade provides for selectively increasing the number of retractor blades forming the operative corridor during (or before) use and prevent tissue creep into the operative corridor from the anterior border. The ability to selectively increase the number of retractor blades affords additional user control over the size and/or configuration of the access corridor, advantageously increasing the versatility of retractor assembly. The supplemental anterior retractor blade includes a blade and a handle. A connecting device cooperates with the supplemental blade and the cephalad and caudal blades to hold the supplemental retractor blade in position. The supplemental retractor blade may be manipulated to manually retract tissue anteriorly. Thereafter the connecting element may be engaged to the retractor blades to hold the supplemental blade in place.

The posterior (center) blade may be coupled to the nerve monitoring system to conduct nerve monitoring during advancement of the retractor assembly and/or during retraction. According to a first embodiment, the blade may be formed of a conductive material (e.g. aluminum) and coated with an insulative coating. A stimulation signal utilized for the nerve monitoring may then be transmitted through the blade and exit into the body tissue through an uninsulated electrode on the distal end. A special set screw, which connects the retractor blade to the nerve monitoring system may be utilized to prevent current shunting. The set screw includes a nonconductive lower end which contacts the retractor body, while the threaded section that contacts the retractor blade is conductive. According to a second embodiment, the blade may be configured to receive and couple to a disposable electrode. The disposable electrode may be, by way of example, plastic part with a conductive trace deposited along the length of the disposable electrode. An exposed area of the conductive trace at a proximal end of the electrode couples with the nerve monitoring system. An exposed area at the distal end of the disposable electrode transmits a stimulation signal from the nerve monitoring system to the tissue adjacent the distal end of the retractor blade. The disposable electrode may couple to engagement features formed in the posterior blade. The disposable electrode may be situated within a channel formed in the blade. The distal end of the posterior blade may include a cut-out that exposes the distal end of the disposable electrode to tissue posterior to the blade. An intradiscal shim for use with the posterior blade/disposable electrode combination may preferably be coated with an insulative coating to prevent current shunting.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 11-12 are front perspective and back perspective views, respectively, of one example of a locking shim forming part of the surgical access system of the present invention;

FIG. 13 is a top view of the locking shim of FIG. 11;

FIGS. 21-24 are exploded and perspective views of a distal pivot member and gear member forming part of the arm member of FIG. 20;

FIG. 25 is a rear perspective view of an anterior retractor blade forming part of the tissue retraction system of FIG. 2;

FIG. 26 is a front perspective view of the anterior retractor blade of FIG. 25;

FIGS. 52-55 illustrate an example of a shim removal tool for use with the locking shim of FIG. 49;

FIG. 56 illustrates a second example of a shim removal tool for use with the locking shim of FIG. 49;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. It is also expressly noted that, although shown and described herein largely within the context of a preferred lateral surgery in the lumbar spine, some or all of the components of the access system described may be employed in any number of other spine surgery access approaches. By way of example, in addition to accessing a lumbar disc space (e.g. for fusion, total disc replacement, corpectomy, etc. . . . ), the surgical access system or some of its components may be used to access the lateral aspect of the thoracic spine (e.g. for fusion, total disc replacement, corpectomey, etc. . . . ), and the posterior spine (e.g. for posterior decompression). By way of further example, it is contemplated that the surgical access system or some of its components may be used to access any of the posterior, postero-lateral, anterior, and anterolateral aspects of the spine, and may be employed in the lumbar, thoracic and/or cervical spine.

The instruments and methods described herein are designed and optimized for creating a lateral access corridor to the lumbar spine. Accessing the targeted spinal site through the lateral access corridor avoids a number of disadvantages associated with posterior access (e.g. cutting through back musculature and possible need to reduce or cut away part of the posterior bony structures like lamina, facets, and spinous process) and anterior access (e.g. use of an access surgeon to move various organs and blood vessels out of the way in order to reach the target site). According to one example, the lateral access approach to the targeted spinal space may be performed according to the methods described in U.S. Pat. No. 7,207,949 entitled "Surgical Access System and Related Methods," and/or U.S. Pat. No. 7,905,840 entitled "Surgical Access System and Related Methods," the entire contents of which are each incorporated herein by reference as if set forth herein in their entireties.

Figure 1:
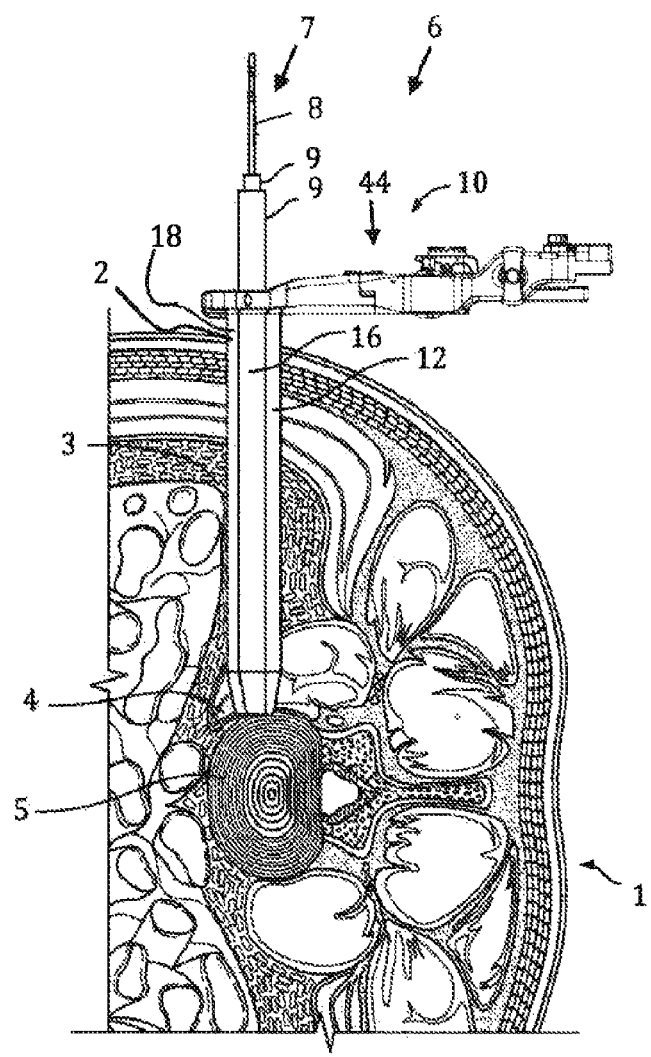
FIG. 1 is a FIG. 3 is a top-down view depicting the creation of a lateral access corridor formed with a surgical access system via a lateral approach through the side of the patient to the target disc space, according to one example embodiment.
Figure 2:
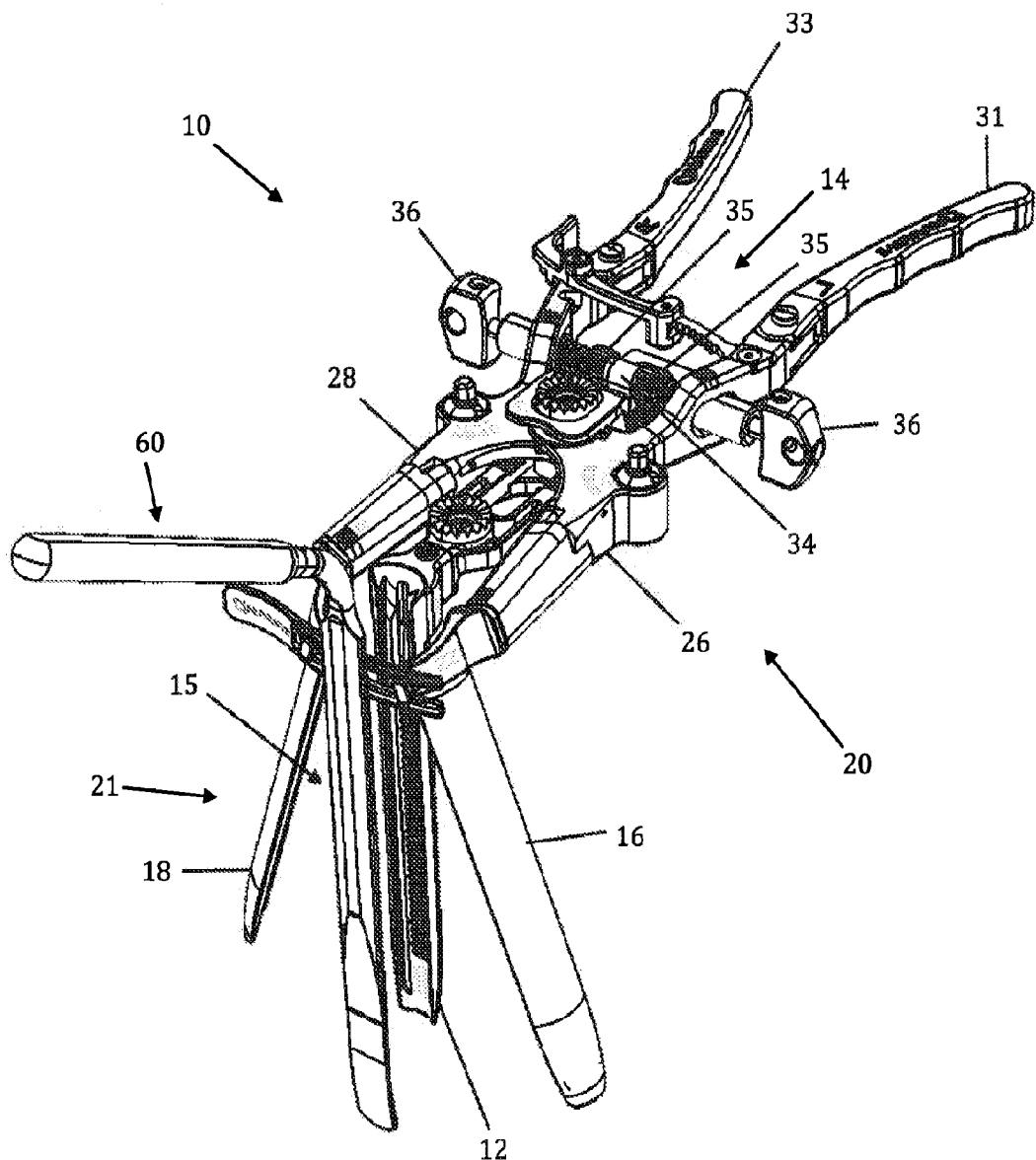
FIG. 2 is a perspective view of one example of a tissue retraction assembly forming part of a surgical access system according to one embodiment of the present invention, shown in a fully retracted or "open" position.
Figure 3:
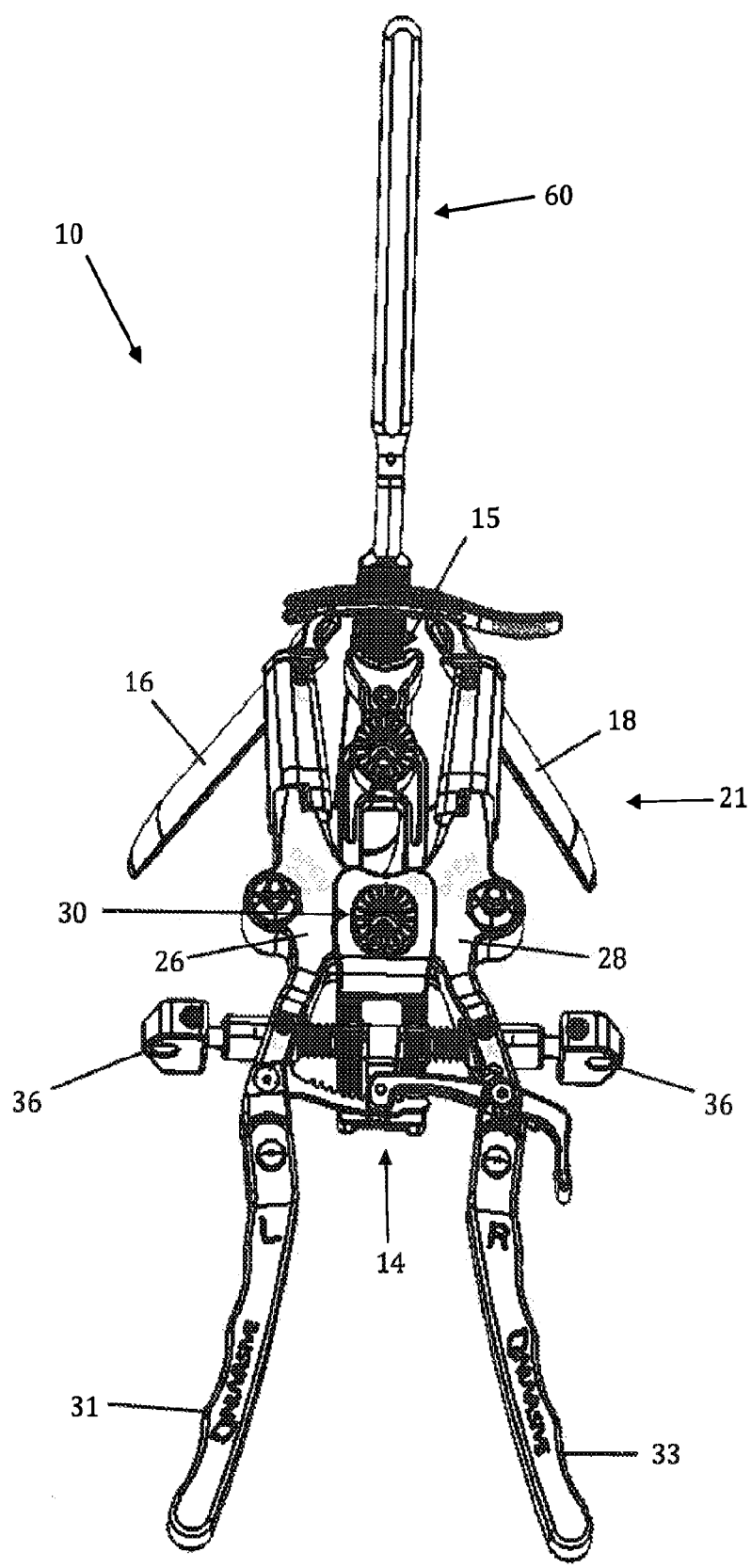
FIG. 3 is a top perspective view of the tissue retraction assembly of FIG. 2, shown in a fully retracted or "open" position.

With reference to FIGS. 1-2, a discussion of the lateral access methods is provided in brief detail. With the patient 1 positioned on their side, a surgical access system 6 is advanced through an incision 2, into the retroperitoneal space 3, and then through the psoas muscle 4 until the targeted spinal site (e.g. the disc space 5 between a pair of adjacent vertebral bodies) is reached. The access system 6 may include at least one tissue dilator, and preferably includes a sequential dilation system 7 with an initial dilator 8 and one or more additional dilators 9 of increasing diameter, and a tissue retractor assembly 10. As will be appreciated, the initial dilator 8 is preferably advanced to the target site first, and then each of the additional dilators 9 of increasing diameter are advanced in turn over the previous dilator. A k-wire (not shown) may be advanced to the target site and docked in place (for example, by inserting the k-wire into the vertebral disc) prior to, in concurrence with, or after advancing the initial dilator 8 to the target site. With the sequential dilation system 7 positioned adjacent the target site (and optionally docked in place via the k-wire), the retractor assembly 10 is then advanced to the target site over the sequential dilation system 7.

According to the embodiment shown, the retractor assembly 10 includes retractor blades 12, 16, 18 and a body 20. According to the preferred method, the retractor assembly 10 is advanced over the dilation system 7 such that the center retractor blade 12 is the posterior most blade. The sequential dilation system 7 is removed and the retractor assembly 10 is operated to expand the operative corridor. That is, the retractor blades 12, 16, and 18 are separated (FIG. 1), providing the lateral access corridor through which instruments and implants may be advanced to the target site. It will be appreciated that any number of procedures may be performed on the spine through the lateral access corridor (e.g. the surgeon may perform a fusion procedure, a total disc replacement, a corpectomy, etc. . . . ). According to one example, the posterior blade 12 may be fixed in position relative to the spine prior to opening the retractor blades. This may be accomplished, for example by attaching a shim to the blade (e.g. via a blade track including dove tail grooves formed on the interior of blade) and inserting the distal end of the shim into the disc space. Alternatively, or in addition, the posterior blade 12 may be fixed in position by connecting an articulating arm between the surgical table (or other suitable mount) and the translating arm associated with the center blade 12). In this manner, the posterior blade 12 will not move posteriorly (towards nerve tissue located in the posterior portion of the psoas muscle). Instead, the blades 16 and 18 will move away from the posterior blade 12 to expand the access corridor.

Additionally, nerve monitoring (including determining nerve proximity and optionally directionality) is preferably performed as each component of the access system 6 is advanced through the psoas muscle, protecting the delicate nerve tissue running through the psoas, as described in the '949 patent and '668 application. Monitoring the proximity of nerves not only allows the surgeon to avoid delicate nerves as the access system is advanced to the spine, but by determining the location of the nerves also allows the surgeon to position the posterior blade more posterior (e.g. all the way back to the exiting nerve roots), thus exposing a greater portion of the target site than would otherwise be safely achievable.

With the lateral access corridor formed the target site may be operated on. For example, when performing a fusion procedure through the lateral access corridor, the disc space 5 may prepped for insertion of an implant. Preparation of the disc space may include performing an annulotomy, removal of disc material, and abrasion of the endplates, and instruments such as annulotomy knives, pituitaries, curettes, disc cutters, endplate scrapers may be used. An implant may be inserted into the disc space. Fusion promoting materials may be implanted within the disc space 5 in and around the implant. Fixation may be performed through the lateral access corridor, or through different approaches.

Figure 4:
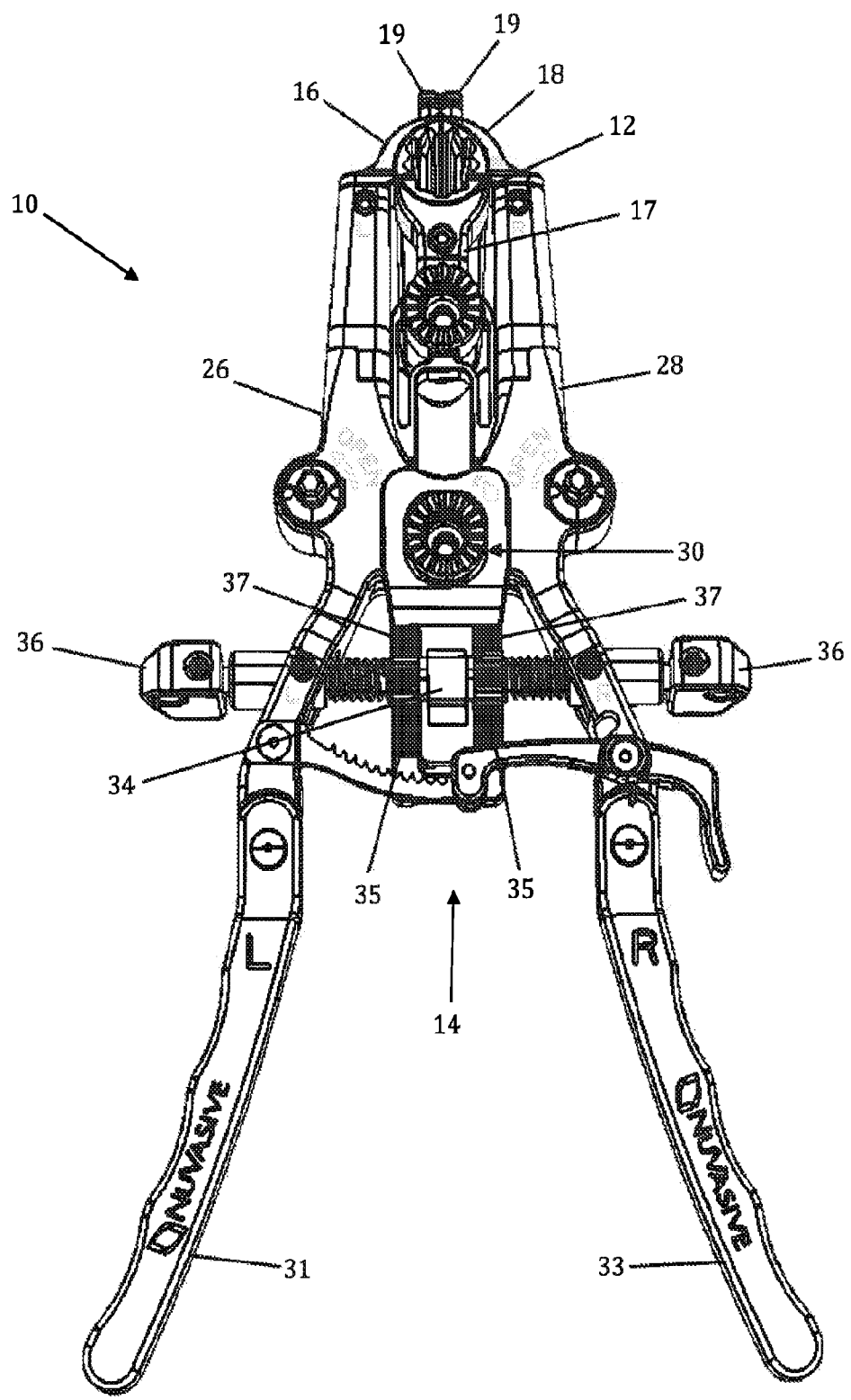
FIG. 4 is a top perspective view of the tissue retraction assembly of FIG. 2 shown in a fully closed position.
Figure 5:
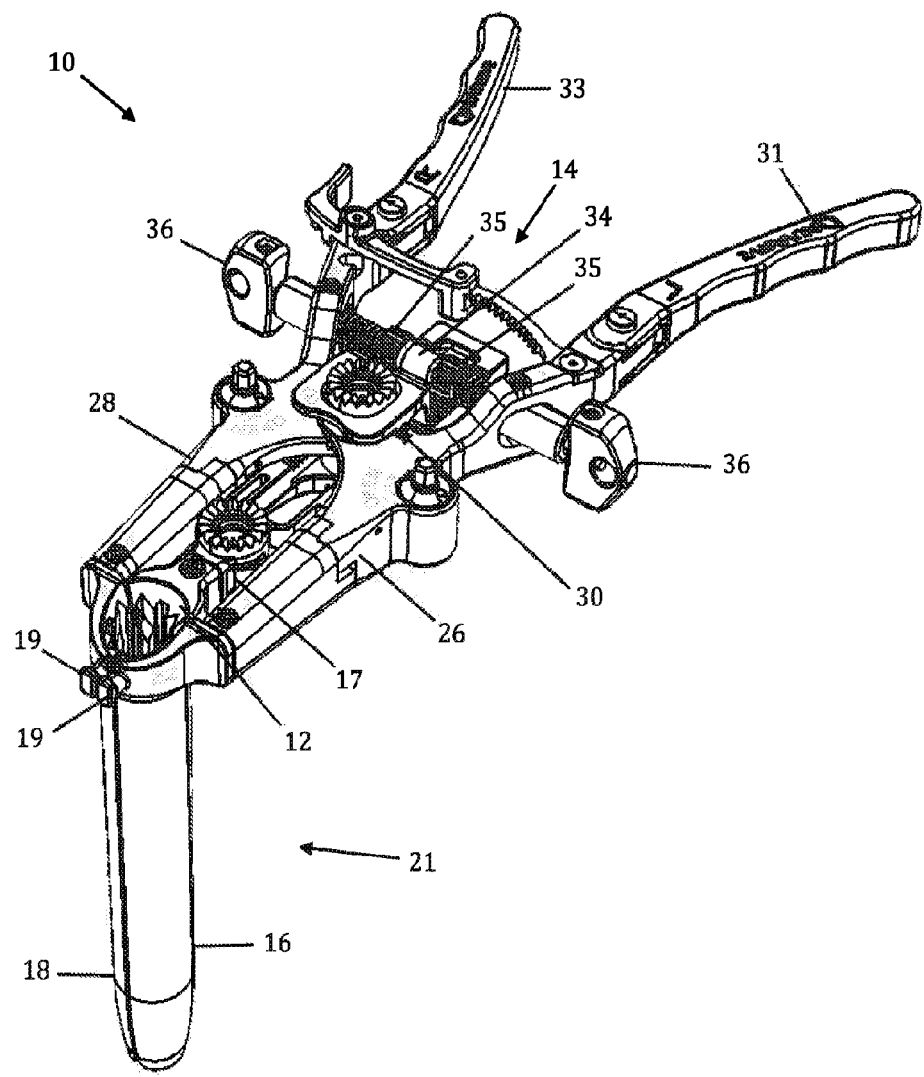
FIG. 5 is a perspective view of the tissue retraction assembly of FIG. 2 shown in a fully closed position.
Figure 6:
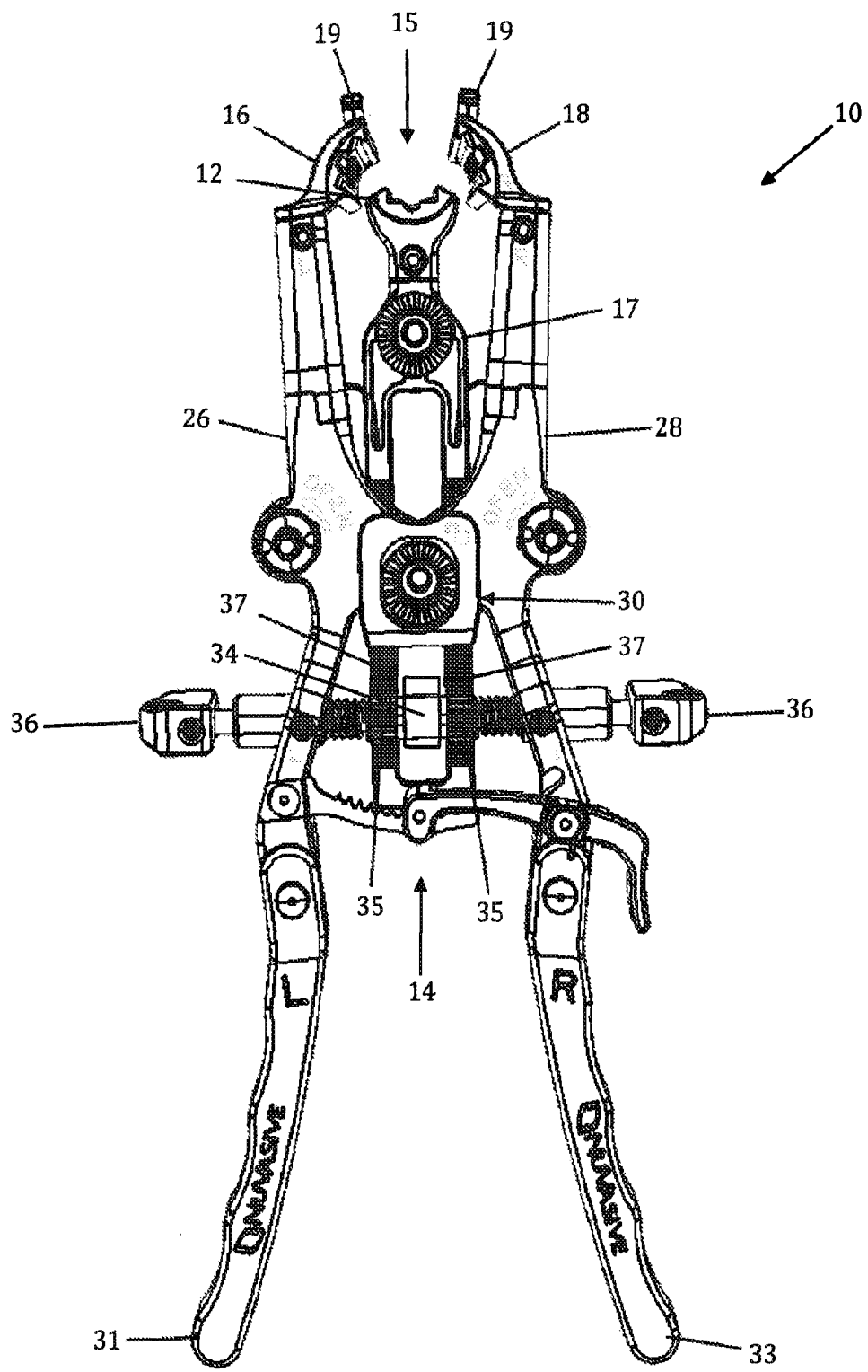
FIG. 6 is a top view of the tissue retraction assembly of FIG. 2 shown in a partially open position according to the present invention.
Figure 7:
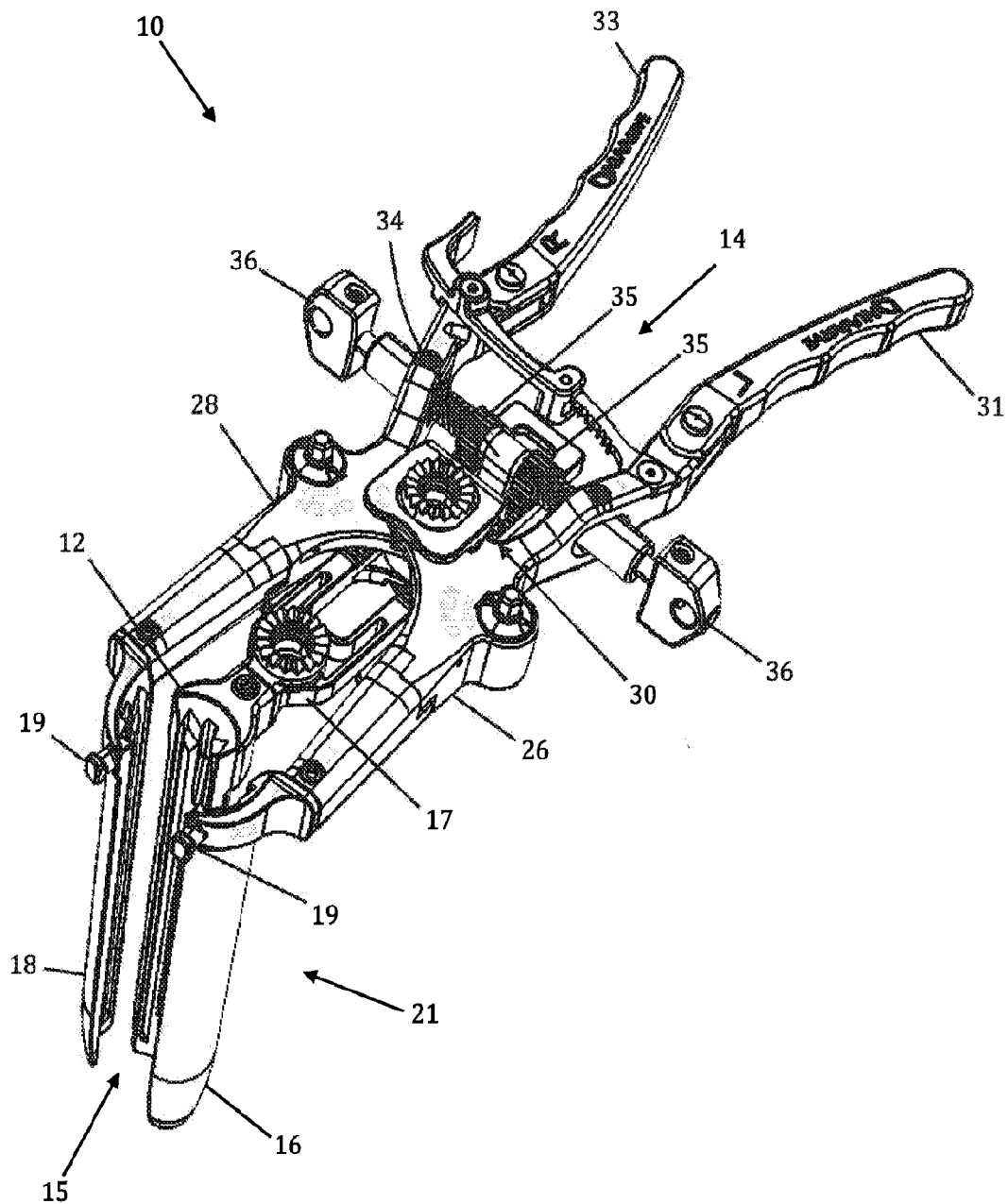
FIG. 7 is a perspective view of the tissue retraction assembly of FIG. 2 shown in a partially open position according to the present invention.

The retraction assembly described herein is well suited for creating the lateral access corridor to the lumbar spine as described above. FIGS. 2-7 illustrate a tissue retraction assembly 10 forming part of a surgical access system according to the present invention, including a plurality of retractor blades 12, 16, 18 extending from a body 20. By way of example only, the body 20 is provided with a first retractor blade 12, a second retractor blade 16, and a third retractor blade 18. FIG. 2 illustrates the tissue retraction assembly 10 in a fully retracted or "open" configuration, with the retractor blades 12, 16, 18 positioned a distance from one another so as to form an operative corridor 15 therebetween which extends to a surgical target site (e.g. an annulus of an intervertebral disc). In one exemplary aspect, the blades 16, 18 are capable of being pivoted or rotated relative to the handle 20, as best appreciated with combined reference to FIGS. 2 & 3. FIGS. 4-5 show the tissue retraction assembly 10 in an initial "closed" configuration, with the retractor blades 12, 16, 18 generally abutting one another. FIGS. 6-7 show the tissue retraction assembly 10 in a "partially open" configuration.

The body 20 may be coupled to any number of mechanisms for rigidly registering the body 20 in fixed relation to the operative site, such as through the use of an articulating arm mounted to the operating table (not shown). The body 20 includes first and second arm members 26, 28 hingedly coupled via coupling mechanism shown generally at 30. The second retractor blade 16 is rigidly coupled (generally perpendicularly) to the end of the first arm member 26. The third retractor blade 18 is rigidly coupled (generally perpendicularly) to the end of the second arm member 28. The first retractor blade 12 is rigidly coupled (generally perpendicularly to) a translating member 17, which is coupled to the body 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Through the use of handle extenders 31, 33, the arms 26, 28 may be simultaneously opened such that the second and third retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, a generally triangular cross-section, and/or an oval cross-section. Optional light emitting devices (not shown) may be coupled to one or more of the retractor blades 12, 16, 18 to direct light down the operative corridor 15.

The retractor blades 12, 16, 18 may be composed of any rigid material suitable for introduction into or around the human body, including but not limited to aluminum, titanium, stainless steel, and/or clear polycarbonate, that would ensure rigidity during tissue distraction. The retractor blades 12, 16, 18 may be optionally coated with a carbon fiber reinforced coating to increase strength and durability. The retractor blades 12, 16, 18 may be optionally constructed from partially or wholly radiolucent materials (e.g. aluminum, PEEK, carbon-fiber) to improve the visibility of the surgeon during imaging (e.g. radiographic, MRI, CT, fluoroscope, etc.). Likewise, the retractor body may be composed of any number of rigid materials, particularly including, but not limited to aluminum, stainless steel, carbon-fiber, and titanium. According to a preferred embodiment, the retractor blades 12, 16, and 18 and body are comprised of stainless steel. The stainless steel has a greater stiffness than other more radiolucent materials (e.g. aluminum) and thus eliminates, or at least reduces, toeing inward (blade flex) of the blades and potential intraoperative breakage. While the stainless steel does not have the radiolucent characteristics of other materials often used for spinal retractors, the added stiffness (in addition to the design of the blade rotation gear 79) permits the body to be constructed with less material. Thus cutouts through the body and reduced geometry of the body permit fluoroscopic visibility through the retractor assembly 10 where necessary, without sacrificing the strength and stiffness of the retractor. By way of example only, the cutouts 17a and 17b and indents 17c of the translating arm 17 allow optimal visualization of pertinent areas (e.g. posterior border of the vertebral bodies in a lateral fluoroscopy image) without sacrificing stiffness. The retractor blades 12, 16, 18 may be provided in any number of suitable lengths, depending upon the anatomical environment and surgical approach, such as (for example) the range from 20 mm to 180 mm. Based on this range of sizes, the tissue retraction assembly 10 of the present invention is extremely versatile and may be employed in any of a variety of desired surgical approaches, including but not limited to lateral, posterior, postero-lateral, anterior, and antero-lateral, by simply selecting the desired size retractor blades 12, 16, 18 and attaching them to the body 20 as will be described herein.

Figure 8:
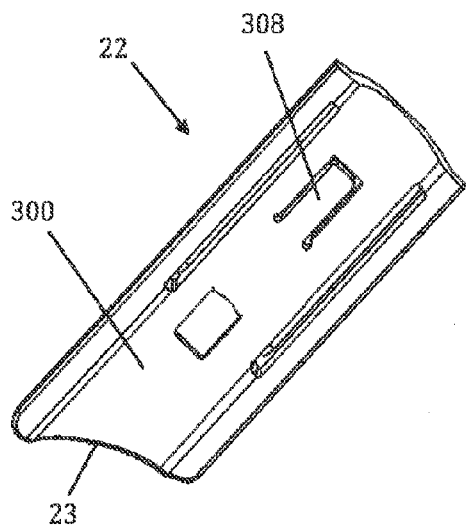
FIGS. 8-9 are perspective views of the front side and back side, respectively, of an example of a contoured shim forming part of the surgical access system of the present invention.
Figure 9:
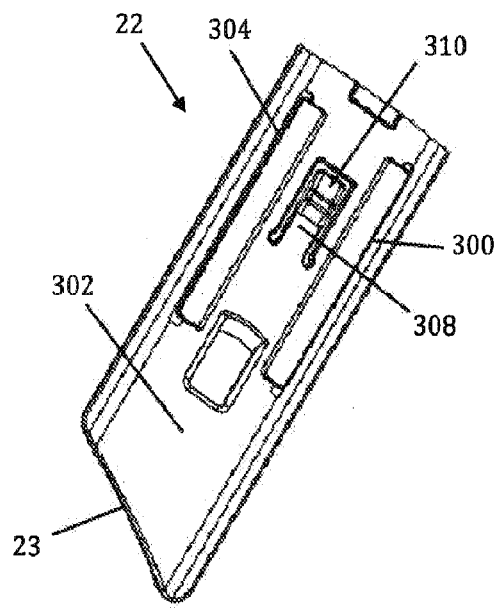
Figure 10:
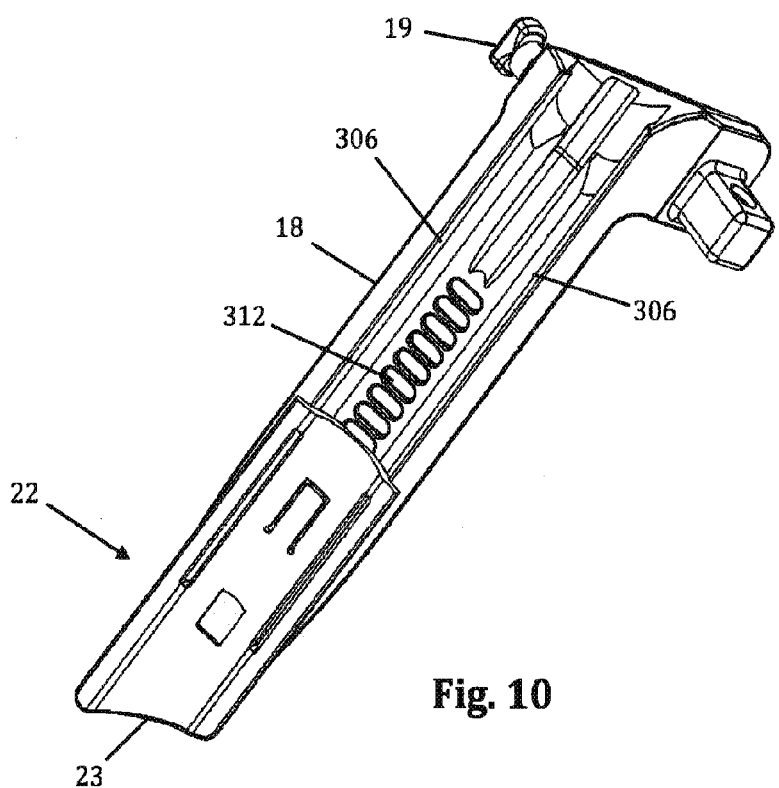
FIG. 10 is an perspective view of the contoured shim of FIG. 8 connected to a retractor blade.
Figure 14:
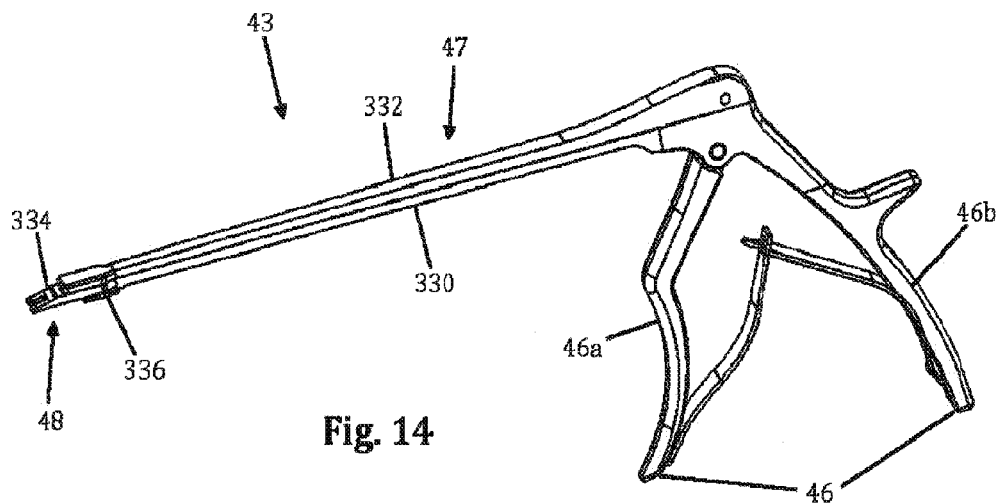
FIG. 14 is a perspective view of an example of a shim removal tool according to one embodiment of the present invention.
Figure 15:
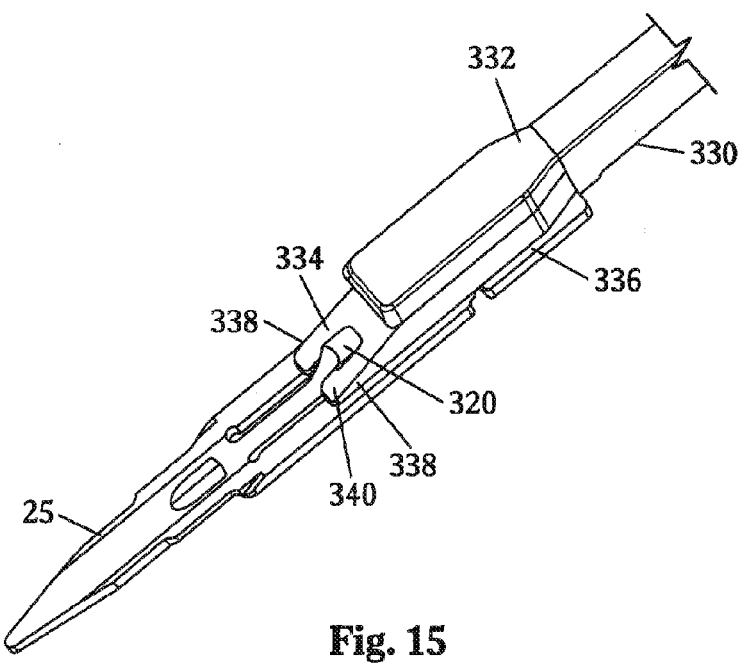
FIG. 15 is a perspective view of the distal portion of the shim removal tool of FIG. 14 engaged with the locking shim of FIG. 11.
Figure 16:
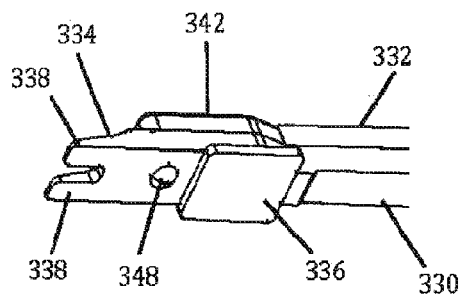
FIG. 16 is a perspective view of the distal portion of the shim removal tool of FIG. 14.
Figure 17:
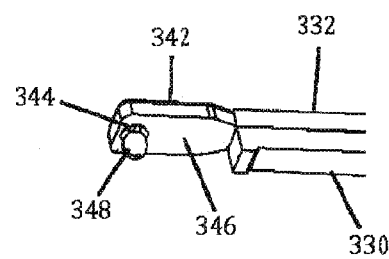
FIG. 17 is a perspective view of the distal portion of the shim removal tool of FIG. 15 with the grip extension removed.

The retractor blades 12, 16, 18 may be equipped with various additional features or components. By way of example only, one or more of the retractor blades 12, 16, 18 may be equipped with a shim, such as a contoured extender shim 22 or a locking shim 25 as shown in FIGS. 8-13. In a preferred embodiment, the contoured extender shims 22 are suitable for engagement with the caudal/cephalad retractor blades 16, 18, while the interdiscal locking shim 25 is suitable for engagement with the center blade 12. However, it should be noted that any shim 22, 25 may be used with any blade 12, 16, 18 without departing from the scope of the present invention. Referring to FIGS. 8-10, the contoured extender shim 22 extends from retractor blades 16, 18 (as shown on one retractor blade 18 in FIG. 10) to form a protective barrier to prevent the ingress or egress of instruments or biological structures (e.g. nerves, vasculature, etc.) into or out of the operative corridor 15. By way of example only, the contoured extender shim 22 includes a front face configured to form a portion of the operative corridor and having a generally concave surface 300. The contoured extender shim 22 further includes a back surface 302 configured to face the retractor blade 18 and having a generally convex shape. The contoured extender shim 22 further has a pair of elongated tab members 304 that are configured to slideably engage elongated slot members 306 that run the length of the inside surface of the retractor blade 18. The contoured extender shim 22 further includes a deflectable tab 308 near the proximal end of the contour extender 22. The deflectable tab 308 includes a knob 310 extending away from the deflectable tab 308 on the back side of the contoured extender shim 22. The knob 310 is configured to engage with indentations 312 positioned along the retractor blade 18 to provide for a lock-stop mechanism securing the contoured extender shim 22 in position during use. In this fashion the contoured extender shim 22 is advanced distally along the retractor blade 18 until a desired position has been reached. The contoured distal end of the contoured extender shim 22 is shaped to conform to the vertebral body to maximize contact with the vertebral body, particularly near the anterior drop, and prevent tissue creep into the exposure. For example, the distal end may have a curved surface such that one longitudinal edge of the contoured extender shim 22 is longer than the other longitudinal edge. For example, the geometry of the distal end 23 allows it to contour to the anterior drop off of the vertebral body as the retractor is opened anteriorly.

Referring to FIGS. 11-13, the locking interdiscal shim 25 has a distal tapered region 45 which may be advanced into the disc space for the purpose of distracting the adjacent vertebral bodies (thereby restoring disc height) and/or anchoring the blade 12 relative to the spine. In similar fashion to the contoured extender shim 22, the locking interdiscal shim 25 also forms a protective barrier to prevent the ingress or egress of instruments or biological structures (e.g. nerves, vasculature, etc.) into or out of the operative corridor 15. The locking interdiscal shim 25 locks in position on the retractor blade 12 to prevent the shim from dislodging and allowing the retractor to move from the targeted location. To lock position on the blade, the shim 25 has a flexible engagement tab 320 with a ramped leading edge 49 that allows it to advance down indentations 312 on the inner surface of the retractor blade 12. The trailing edge 27 of the engagement tab 320 is squared to prevent disengagement (thus preventing unwanted backout of the shim) from the indentation 312 without use of a removal tool 43. The engagement tab 320 also includes a T-shaped removal lip 55 configured to engage a shim removal tool, as described below. The T-shaped lip 55 of the engagement tab 320 allows the removal tool 43 to lift the square lip 27 away from the retractor blade 12 and remove the shim 25. The locking interdiscal shim 25 has a pair of elongated tab members 322 that are configured to slideably engage elongated slot members 306 that run the length of the inside surface of the retractor blade 12. The locking interdiscal shim 25 includes a dimple or aperture 56 located near the proximal end of the shim 25 configured for engagement with a shim removal tool, as will be explained in further detail below.

FIGS. 14-17 illustrate an example of a shim removal tool 43 for extracting the locking interdiscal shim 25 from a retractor blade 12, which in the example provided resembles a Kerrison-style removal tool. By way of example only, removal tool 43 is shown and described herein in conjunction with locking interdiscal shim 25, although it is to be readily appreciated that removal tool 43 may be employed in a similar manner with other locking shims without departing from the scope of the present invention. The removal tool 43 includes a squeezable handle 46, an elongated region 47 including a stationary arm 330 and a translating arm 332, and a distal end 48. The squeezable handle 46 includes a front handle 46a and back handle 46b. The front handle 46a is pivotably connected to the translating arm 332, while the back handle 46b is immovably connected to the stationary arm 330. The distal end 48 includes a grip extension 334 configured to interact with both the retractor blade 12 and the interdiscal locking shim 25. The grip extension 334 includes a track guide 336 that slideably engages the elongated slot members 306 as described above in relation the shims 22, 25. The distal end of the grip extension 334 includes a pair of arms 338 extending distally from the grip extension 334 in a generally parallel fashion. The arms 338 include a ramped surface 340 sloped such that the thickness of the arms 338 at their distal ends is considerably less than the thickness of the arms 338 at their proximal ends where they extend from the grip extension 334. The ramped surface 340 may be planar or have a concave curvature without departing from the scope of the present invention. The distal end of the translating arm 332 includes a translating plate 342. The translating plate is generally planar and includes a dimple or recess 344 positioned on the lower surface 346 of the translation plate 342. The recess 344 is configured to receive a locking ball 348 when the removal tool 43 is in a neutral position (i.e. when the handles 46a, 46b are released).

To use the removal tool 43, the distal end 43 including the grip extension 334 is slideably advanced along the retractor blade 12 with the handle 46 in the neutral position until the ramped arms 338 engage the removal lip 55 of the shim 25. When the handle 46 is in the neutral position, the locking ball 348 retreats into the recess 344 of the translating plate 342 allowing the distal end 48 of the grip extension 334 to engage flush with the shim 25. When the ramped arms 338 engage the removal lip 55 of the interdiscal locking shim 25, the lip 55 is deflected outward lifting the engagement tab 320 away from the retractor blade 12. Simultaneously, the locking ball becomes positioned in the aperture 56 of the locking shim 25. Squeezing the front handle 46a causes the translating arm 332 to slideably translate forward relative to the stationary arm 330. This translates the position of the recess 344 on the translating plate 342 such that the locking ball 348 is prevented from entering the recess 344. With the locking ball positioned within aperture 56, the removal tool 43 is now locked to the locking shim 25 such that the shim 25 may be removed by applying a force in a proximal direction relative to the retractor blade 12. Thus, squeezing the removal tool handle 46 locks the distal end 48 to the interdiscal locking shim 25 while disengaging the the lip 55 of the engagement tab 320 from the indentation. 312 of the retractor blade 12, enabling the user to pull up and remove the shim.

Shim elements 22, 25 may be made from any rigid material suitable for use in the human body, including but not limited to biologically compatible plastic and/or metal (such as aluminum, PEEK, carbon-fibers and titanium). According to one example, the extender shims 22 may be made from plastic and the interdiscal shim 25 may be made of metal. The interdiscal shim 25 may also be coated with an insulative coating (e.g. a parylene coating) to prevent current shunting or density changes from electrodes situated at the distal end of the retractor blade 12. Retractor extender shim 22 may have symmetric narrow configurations (FIGS. 8-9), which do not extend laterally from the retractor blade, and/or broad configurations (not shown) that extend laterally from each side of the retractor blade, and/or an asymmetric configuration (not shown) which extends laterally from one side of the retractor blade. The shim elements 22, 25 may be composed of a material that would destruct when autoclaved (such as polymer containing a portion of glass particles), which may be advantageous in preventing the unauthorized re-use of the retractor extender shim 22 and/or the shim element 25 (which would be provided to the user in a sterile state).

Figure 18:
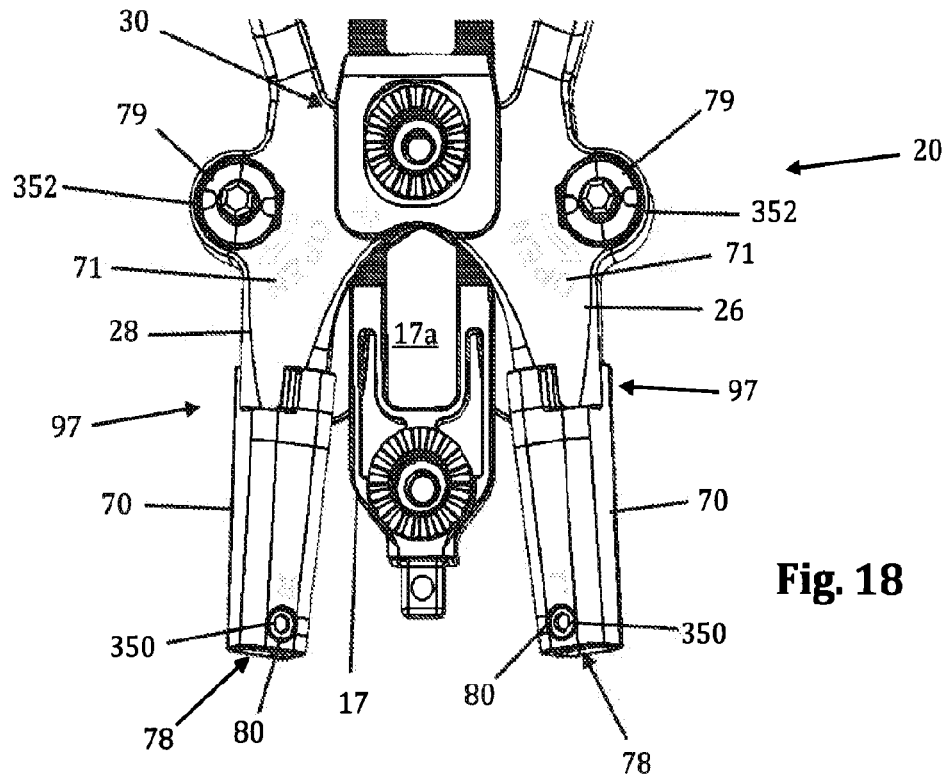
FIG. 18 is a top plan view of the arms of the tissue retraction assembly of FIG. 2.
Figure 19:
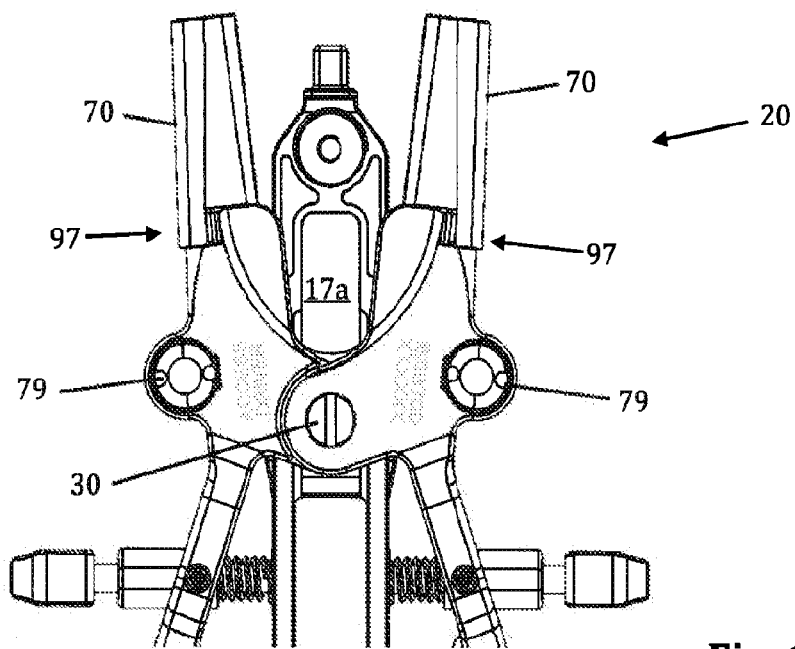
FIG. 19 is a bottom plan view of the arms of the tissue retraction assembly of FIG. 2.
Figure 20:
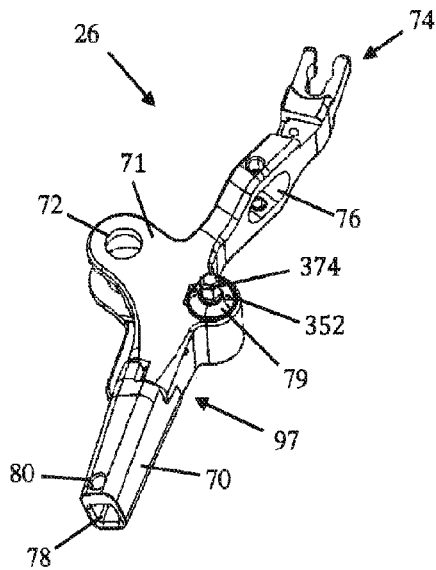
FIG. 20 is a perspective view of an arm member comprising part of the tissue retraction assembly of FIG. 2.

Referring now to FIGS. 18-24, the mechanisms associated with the arm members 26, 28 will be discussed in further detail. Although the inventive features will be discussed in relation to the first arm member 26 only, it should be understood that the second arm member 28 is virtually a mirror image of the first arm member 26 such that features shown and described with respect to the first arm member 26 may be present with respect to the second arm member 28 without departing from the scope of the present invention. Referring first to FIGS. 18-19, the distal region of the body 20 is shown in greater detail. Each arm member 26, 28 includes a distal pivot member 70 and a proximal arm portion 71. Referring also to FIG. 20, which shows the first arm member 26 in greater detail, the distal pivot member 70 extends distally from the proximal arm portion 71 and includes portions of the rotating gear mechanism 79 (described in detail below) housed within the proximal arm portion 71. This position of the gear mechanism proximal to the retractor blades and operative corridor allows the blades to be splayed without inhibiting visualization of the corridor during adjustment. The proximal arm portion 71 includes a coupling aperture 72 through which the coupling element 30 passes, a proximal attachment region 74 at which handle extender 31 may be attached, an aperture 76 through which knob 36 passes, and a gear aperture 352 configured to allow passage of the upper cap 364 and post head 374 of the gear mechanism 79 to allow for accessibility of post head 374 to impart rotation of the retractor blades. The body 20 further includes a restrictor element 97 formed by portions of the distal pivot member 70 and the proximal portion 71 working in concert to restrict the degree of allowable angulation for the retractor blades. At the distal end of the distal pivot member 70 is a blade aperture 78 and a screw aperture 80. The blade aperture 78 is configured to receive an attachment post of the retractor blade 16, 18 to couple the blade to the body 20. The screw aperture 80 threadably receives a setscrew 350 for reversibly securing the retractor blade 16, 18 to the body 20. Translating member 17 is shown by way of example only as having a large viewing aperture 17a which functions to increase visibility during fluoroscopy.

Figure 21:
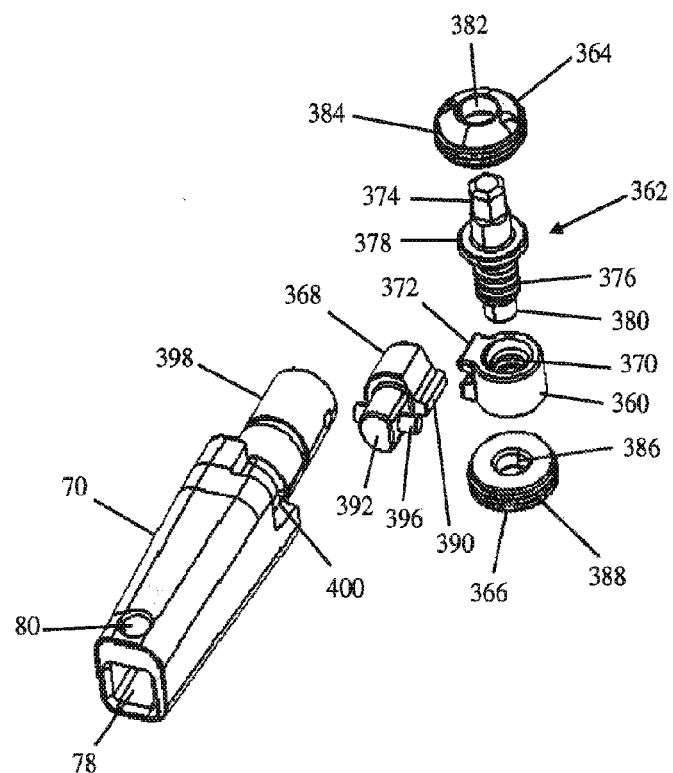
Figure 27:
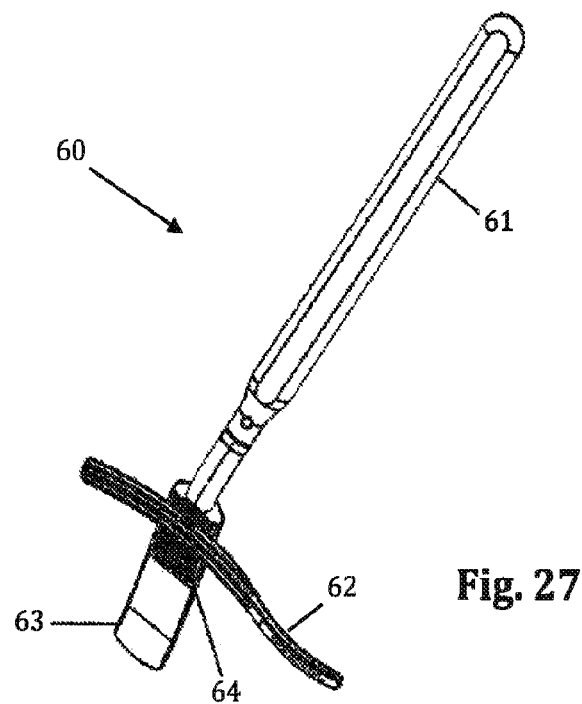
FIG. 27 is a top perspective view of the anterior retractor blade of FIG. 25.
Figure 28:
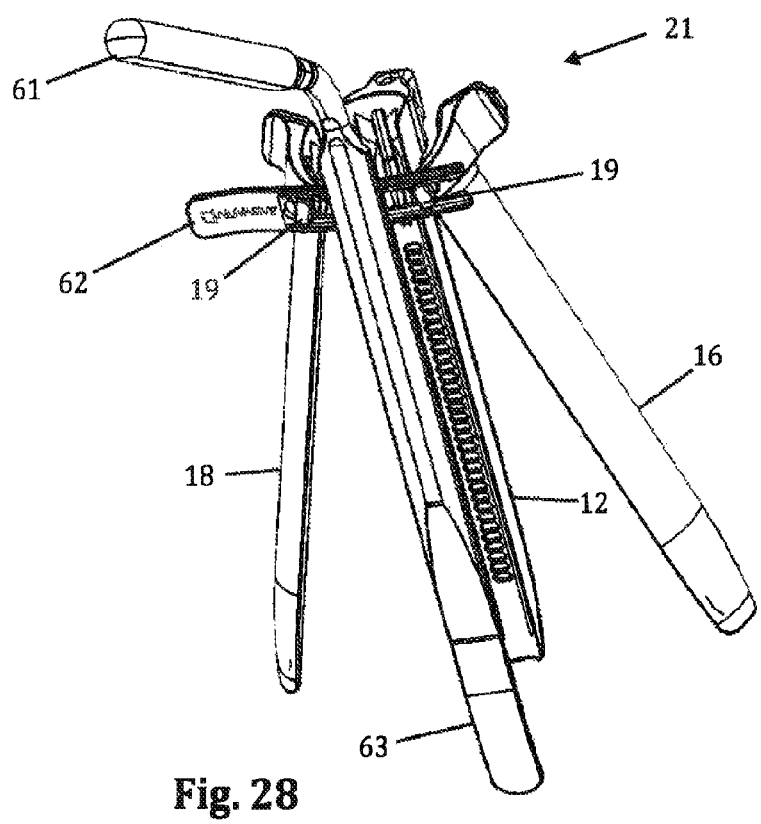
FIG. 28 is a perspective view of the blade assembly portion of the tissue retraction system of FIG. 2 with the anterior retractor blade of FIG. 25 attached thereto.

FIGS. 21-24 illustrate and example of the gear mechanism 79 of the distal pivot member 70 in greater detail. The gear mechanism generally comprises a lead screw driven rack and pinion gear including a translating rack (translating gear 360) and a section gear rotating pinion (rotating gear 368). By way of specific example, the gear mechanism 79 includes a translating gear 360, a lead screw 362, an upper cap 364, a lower cap 366 and a rotation gear 368. The translating gear 360 includes a central threaded aperture 370 extending therethrough and gear teeth 372 oriented generally horizontally on the outside surface. The lead screw 362 includes post head 374, a threaded region 376, a circumferential ridge 378 positioned between the post head 374 and the threaded region 376, and a non-threaded foot 380. The post head 374 may be configured in any shape desirable to engage a rotation tool to effect rotation of the lead screw, including but not limited to the hexagonal shape shown by way of example only in. FIG. 21. The threaded region 376 is configured to engage with the threaded aperture 370 of the translating gear 360. As will be described in detail below, during operation the translating gear 360 translates linearly along the threaded region 376 of the lead screw 362. The upper cap 364 has a generally circular cross-section and includes a central open aperture 382 configured to receive the post head 374 therethrough and circumferential threads 384 configured to threadedly secure the upper cap 354 to the arm member 26. The lower cap 366 includes a central closed aperture 386 configured to receive the foot 380 of the lead screw 362 therein and circumferential threads 388 configured to threadedly secure the lower cap 366 to the first arm member 26. The rotation gear 368 includes at least one horizontal gear tooth 390 extending laterally therefrom and a connector post 392 extending distally therefrom. The horizontal gear tooth 390 engages with the gear teeth 372 of the translating gear 360. The connector post 392 is received within an aperture 394 within the distal pivot member 70. A pin 396 is further provided to secure the connector post 392 to the distal pivot member 70.

In use, a user engages a rotation tool to the post head 374 and rotates in a clockwise direction. This causes the lead screw 362 to rotate. According to one example, the rotation tool may include a torque limiting feature to prevent loading of the retractor blades should they become stuck on bone (e.g. osteophytes) or features. The lead screw 374 bottoms out in the closed aperture 386 of the lower cap 366. The ridge 378 engages with the lower surface of the upper cap 364 ensuring that the lead screw 374 is only able to rotate without any translational movement. Due to the threaded engagement with the translating gear 360, rotation of the lead screw 362 causes the translating gear 360 to translate linearly along the lead screw. Interaction between the gear teeth 372 of the translating gear 360 and the gear teeth 390 of the rotating gear 368 cause the rotating gear 368 to rotate. Because the rotation gear 368 is securely fastened to the distal pivot member 70 via the interface between the connector post 392 and aperture 394, this action in turn causes the distal pivot member 70 to pivot. FIG. 24 illustrates the directional movement of the various parts.

The distal pivot member 70 includes an extension 398 in which the aperture 394 is located, and a recess 400 extending partially around the outside edge of the distal pivot member 70. The recess 400 forms part of the restrictor element 97 and is wider than the corresponding extension on the arm 26 that it receives therein. When the distal pivot member 70 rotates, contact between the extension and the wall of the recess 400 prevents further movement. Thus, the size of the recess 400 and/or extension can be set such that blade splay or rotation is contained within a desired range. By way of example only, this range may be between 0 and 20 degrees. However, a larger range of angulation may be possible without departing from the scope of the invention, for example range of 0-30 degrees and 0-45 degrees are also contemplated.

Initially, the retractor assembly 10 of the present invention is introduced to the surgical target site with the retractor blades 12, 16, 18 in a first, fully closed position (shown generally in FIGS. 4-5). In this configuration, the retractor blades 16, 18 are oriented in a generally perpendicular configuration. In some instances it may be desirable to pivot either the second retractor blade 16 or the third retractor blade 18 (or both) outward in order to increase the volume of the operative corridor 15 (by increasing the distal dimension of the operative corridor). To accomplish this (with respect to blade 16), a female hexagonal driver is engaged to the post head 374 of first arm 26. When the post head 374 is rotated in a clockwise direction, the blade 16 will pivot in a lateral (outward) direction. When rotating the post head 374 in a counter-clockwise direction, the blade 16 will pivot a lateral (inward) direction. The blade splay mechanism 79 employed provides for continuous splay (i.e. may be splayed to any angulation from 0 degrees to a maximum permissible angulation). According to the preferred example, a restrictor element 97 prevents angulation above a maximum permissible angle. For example, the maximum permissible angle may be 20 degrees. The restrictor element may also permit the blade from splaying inward past 0 degrees.

The blade 18 may be pivoted independently of blade 16 such that different angles for each blade 16, 18 are achieved. Thus, it may be desirable to use blades of differing lengths and still maintain a symmetrical operating corridor wherein the distal ends of blades 16, 18 are oriented along the same general plane. Before removing the tissue retraction system 10 from the operative corridor, the post head 374 should be rotated in a counter-clockwise direction, allowing the retractor blade 16 to return to their initial alignment (i.e., generally perpendicular to the handle 20) to facilitate removal. It will be appreciated that the direction of rotation could be reversed by simply reversing the thread direction on the actuating screw and translation gear. Furthermore, although the upper cap 364 and lower cap 366 have been described as being secured to the arm 26 via a threaded engagement, any type of engagement is possible, including but not limited to welding, press-fit, and the like.

Referring to FIGS. 25-28, a supplemental anterior retractor blade 60 may be provided for optional use with the tissue retraction assembly 10 described herein. Supplemental anterior retractor blade 60 provides for selectively increasing the number of retractor blades forming the operative corridor during (or before) use. The ability to selectively increase the number of retractor blades affords additional user control over the size and/or configuration of the access corridor, advantageously increasing the versatility of retractor assembly 10. Although supplemental anterior retractor blade 60 is shown and described herein in use with a three-bladed configuration of the retractor assembly 10 (thereby comprising a fourth retractor blade as referenced herein), it is to be readily appreciated that the supplemental anterior retractor blade 60 may be used with a retractor assembly 10 configured with any number of primary retractor blades.

Figure 29:
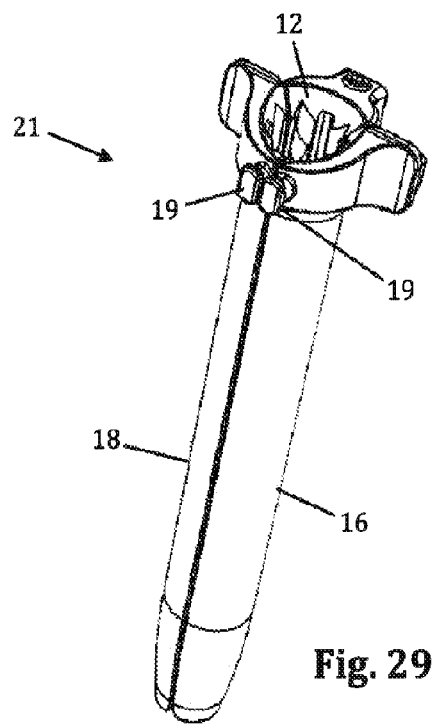
FIG. 29 is a front perspective view of the blade assembly portion of the tissue retraction system of FIG. 2 shown in a fully closed position.
Figure 30:
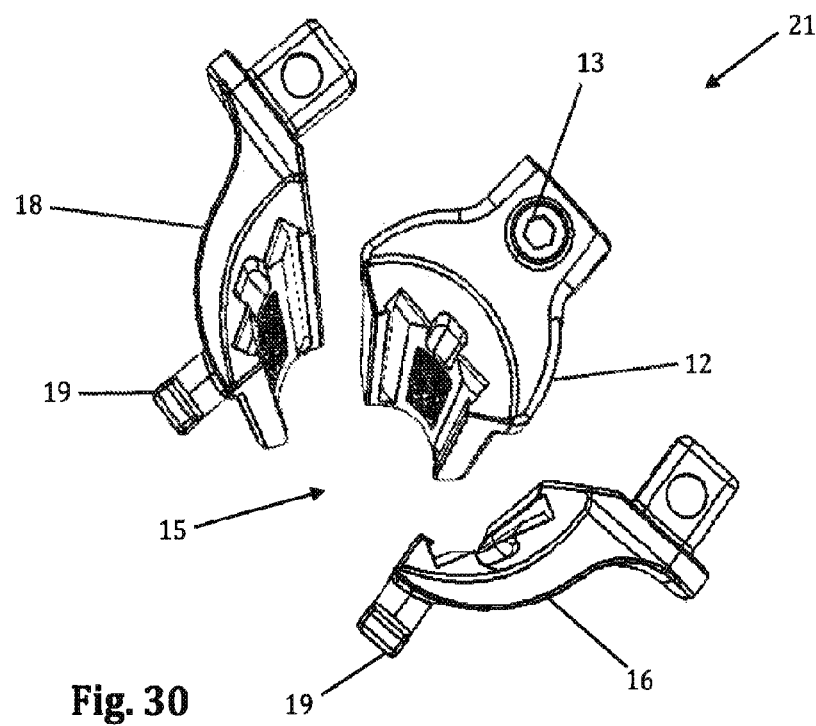
FIG. 30 is a top perspective view of the blade assembly portion of FIG. 29 shown in a partially open position.

As illustrated in FIGS. 25-28, supplemental anterior retractor blade 60 comprises a handle 61, a connecting device 62, a grooved area 64, and a blade 63. The supplemental anterior retractor blade 60 is connected to retractor blades 16, 18. The connecting device 62 slidably interlocks with the holding knobs 19 (FIGS. 29-30), and the retractor blades 16, 18 can move freely (i.e., "open" and "close") while the connecting device 62 remains interlocked with the holding knobs 19. The wider end of the holding knobs 19 prevent the connecting device 62 from becoming disconnected. The grooved area 64 of the anterior retractor blade 60 interlocks with the connecting device at the desired depth. The anterior retractor blade may be made from any rigid material suitable for use in the human body, including but not limited to biologically compatible plastic and/or metal (such as aluminum, PEEK, carbon-fibers, stainless steel, and titanium). The anterior retractor blade 60 may be provided in any number of suitable lengths, depending upon the anatomical environment, surgical approach, and length of primary retractor blades 12, 16, 18, such as (by way of example only) the range from 20 mm to 180 mm.

With reference to FIG. 2, a preferred method of using supplemental blade assembly 60 in conjunction with retractor assembly 10 is shown. The retractor assembly 10 is first advanced to the target site (after tissue distraction) and an initial operating corridor is formed according to the methods described above (i.e. moving retractor blades 16, 18 from a "closed" position to a "retracted" position). Once the operating corridor is created with primary retractor blades 12, 16, 18, the supplemental anterior retractor blade 60 may be utilized to expand the operating corridor and/or provide an extra barrier to prevent ingress of body tissue into the corridor. To do so, the connecting device 62 is slidably secured onto the holding knobs 19, and the grooved area 64 then interlocks with the connecting device. This, along with the pressure of the tissue, holds the anterior retractor blade in position. Preferably, when retracting the tissue, the connecting device 62 is used as a fulcrum and the handle 61 is pulled like a lever inward (i.e., towards the retractor assembly 10) and the distal end of the blade will pivot at an outward angle along the x-axis.

FIGS. 32-35 illustrate an example of a contemplated alternative embodiment to the translating arm 17 which could be replace the translating arm 17 on the retractor assembly 10. The alternative translating arm 91 forms a posterior translation mechanism 90, illustrated in FIGS. 32-35. The posterior translation mechanism 90 permits controlled posterior translation when desired, without the compromising the position of the retractor body in other directions (i.e., caudal-cephalad alignment). By way of example only, the posterior translation mechanism 90 allows for the surgeon to change the position of the blade assembly 21 inside of the surgical site without changing the size of the incision. The wrench 93 secures onto the hexagonal locknut 92 at the distal end, which is a female hexagonal shape 94. Turning the wrench handle 95 clockwise loosens the hexagonal locknut 92, which loosens the connection between the center translating arm 91 and the articulating arm attachment 96. This allows the retractor assembly 10 to be posteriorly translated up to a maximum length of the posterior translation slot (e.g. up to 10 mm in this example) with respect to the articulating arm attachment 96 by pulling the retractor assembly 10 posteriorly. The hexagonal locknut 92 must be fastened after posterior translation. Thus, if a surgeon loses alignment during surgery, he or she can realign the retractor assembly 10 posteriorly with ease and safety.

FIGS. 36-39 illustrate an example of an articulating arm attachment 100 according to one embodiment of the present invention. The articulating arm attachment 100 includes a quick align feature for preliminary engagement of a toothed connector. This feature provides the physician with the means to properly and securely align the teeth (i.e., peaks and valleys) of the connector for intersection single handledly. This feature avoids locking the connectors together before their teeth are properly aligned. This can happen when the teeth become worn and it is more difficult to align the peeks of one connector in the valleys of the other connector.

Figure 38:
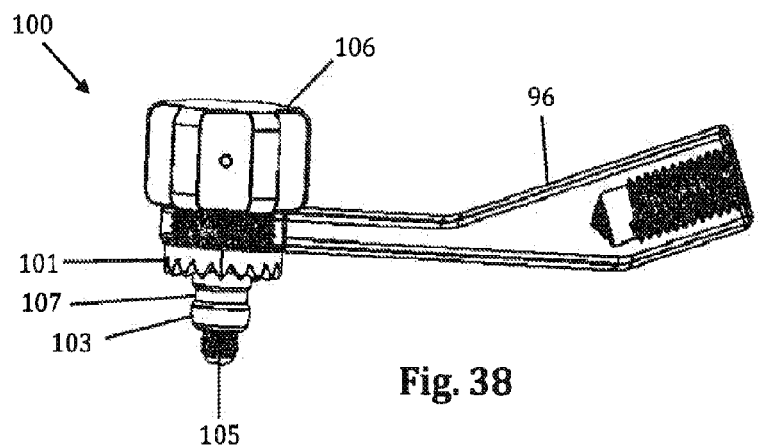
Figure 39:
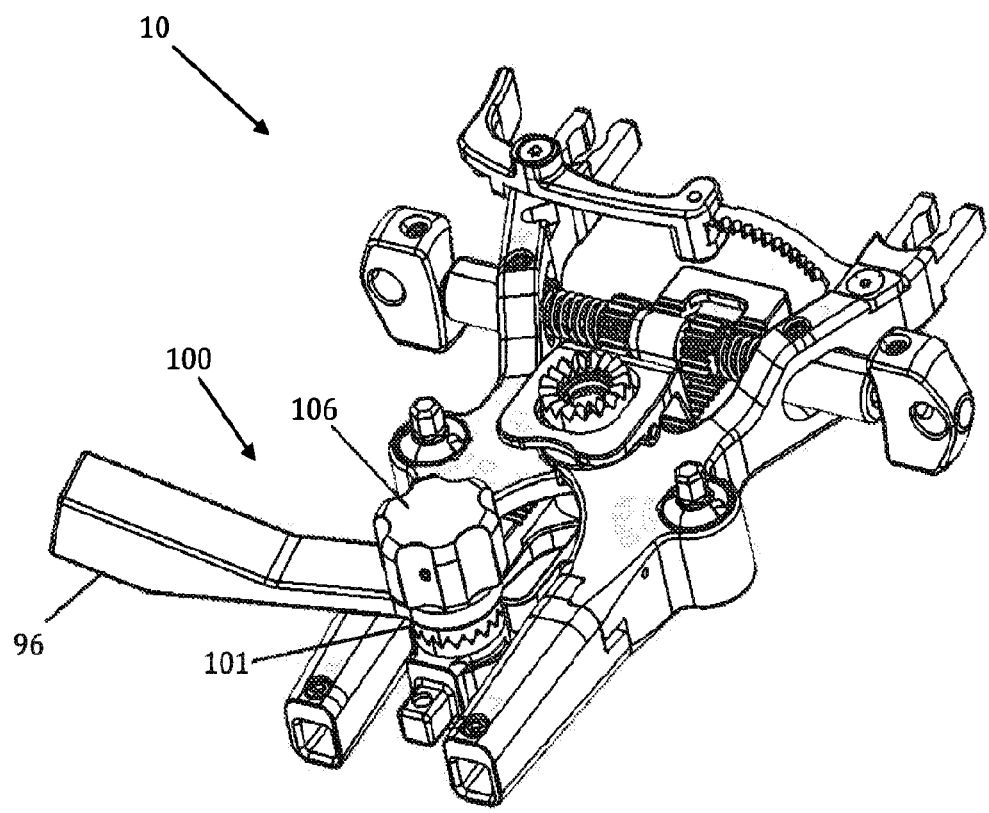
FIG. 39 is a top perspective view of the tissue retraction assembly of FIG. 2 engaged with an attachment arm of FIG. 35.

The quick align articulating arm attachment 100 comprises a superior toothed connector 101, an inferior toothed connector 102, a post 103, and a canted coil ring 104. The canted coil ring 104 rests snugly inside a groove formed in the inferior connector 102. The post 103 screws into and locks onto the inside of the superior connector 101. The post 103 contains a thicker distal end. When connecting toothed connectors 101, 102, the distal end of the post 103 pushes through the canted coil ring 104, which expands to allow the distal end of the post 103 to pass through, and then contracts where the post 103 tapers into a groove 107 (FIG. 38). When the post 103 is pushed through the canted coil ring 104, and the coil contracts, the connectors 101, 102 are semi-secured in place. The post 103 is of the proper length that it will only be semi-secured in place when the teeth of the connectors are properly aligned. The connectors 101, 102 can be disconnected (i.e., pull the post 103 out of the canted coil ring 104) with a moderate effort. By way of example only, to connect the arm attachment 96, the knob 106, which connects to an elongated screw 105, secures the arm attachment to the assembly by screwing the screw 105 into the inferior connector 102, which contains grooves that the screw 105 secures into. While shown for use with an articulating arm and the toothed connector assembly of the retractor assembly 10, the quick align connector 100 is suitable for use with any toothed connector assembly.

Figure 31A:
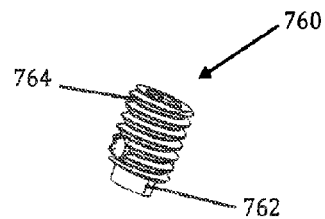
FIG. 31A is a perspective view of a setscrew used to attach the posterior retractor blade to the tissue retraction system of FIG. 2.
Figure 31B:
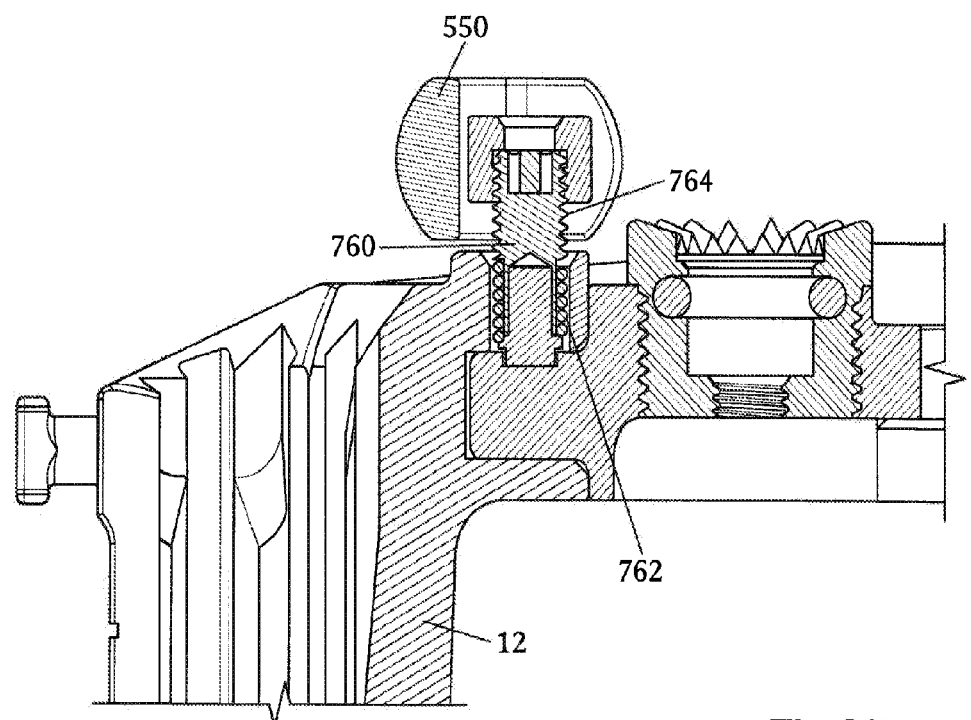
FIG. 31B is a side cross section view of the set screw of FIG. 31A couple to the retractor assembly of FIG. 2.
Figure 32:
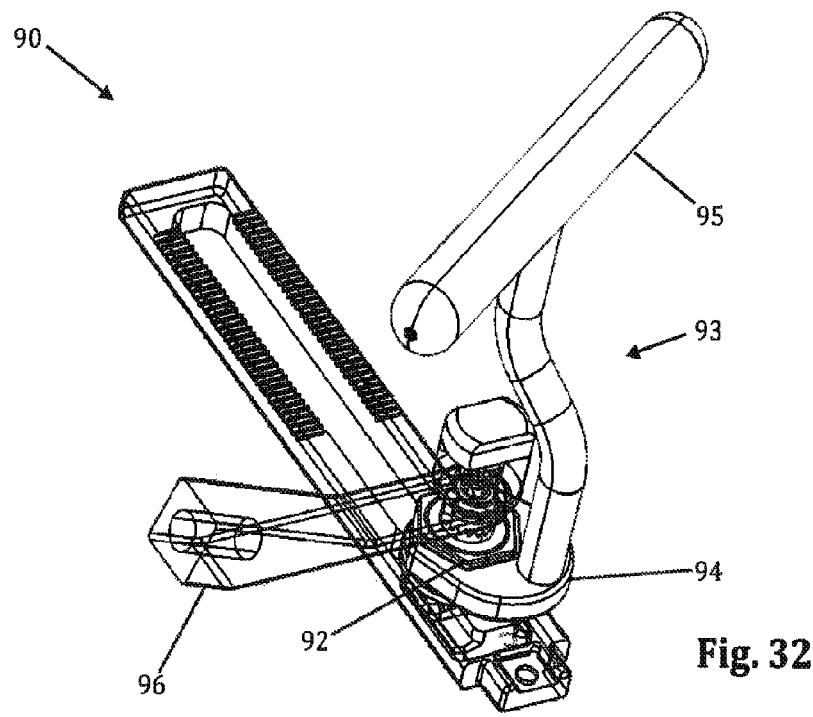
FIG. 32 is a top perspective view of a posterior translation mechanism forming part of the tissue retraction system FIG. 2, engaged with a wrench and attachment arm according to one aspect of the present invention.
Figure 33:
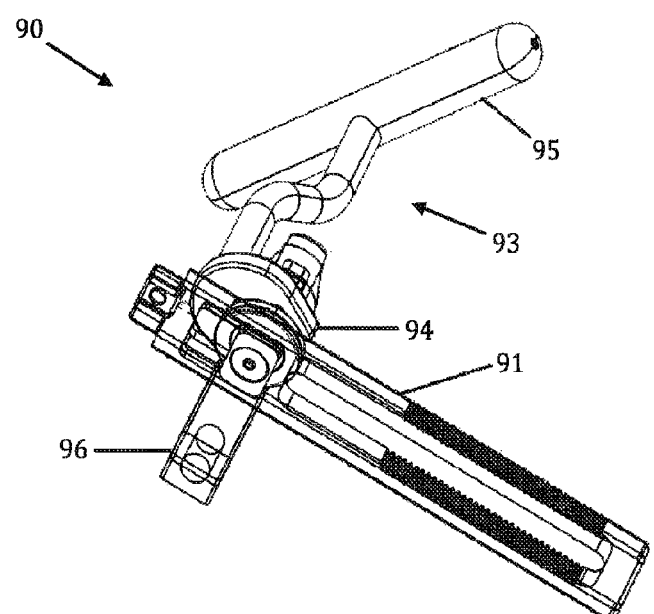
FIG. 33 is a bottom perspective view of the posterior translation mechanism of FIG. 32.
Figure 34:
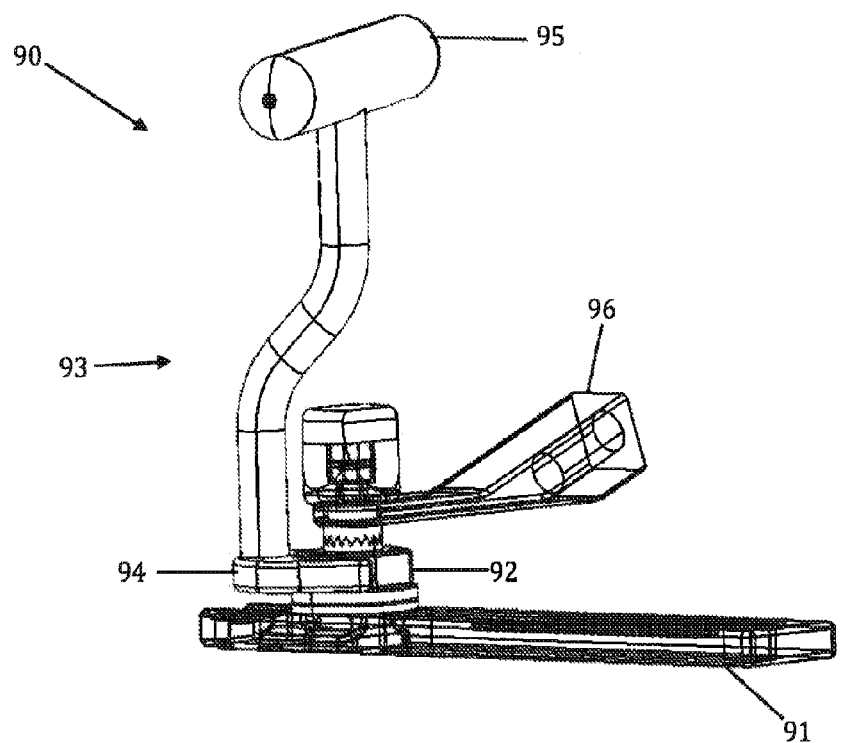
FIG. 34 is a side perspective view of the posterior translation mechanism of FIG. 32.
Figure 35:
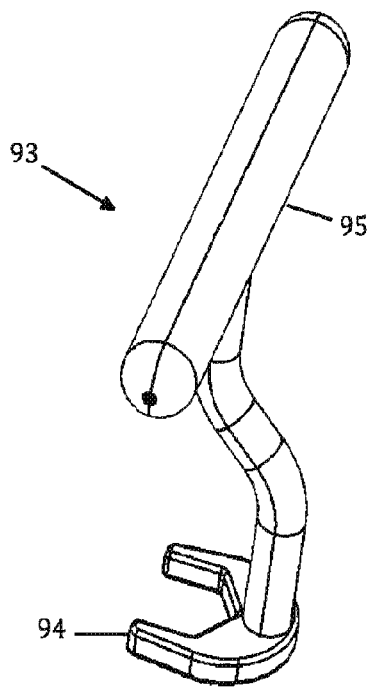
FIG. 35 is a perspective view of the wrench of FIG. 32.
Figure 36:
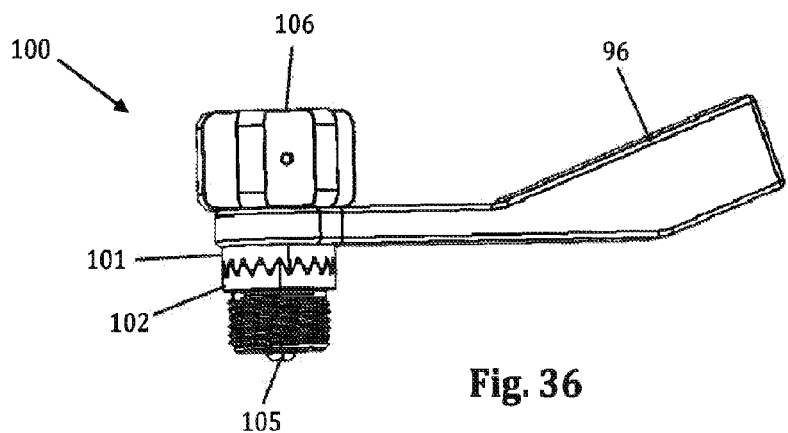
FIGS. 36-38 are side views of the attachment arm of FIG. 32.
Figure 37:
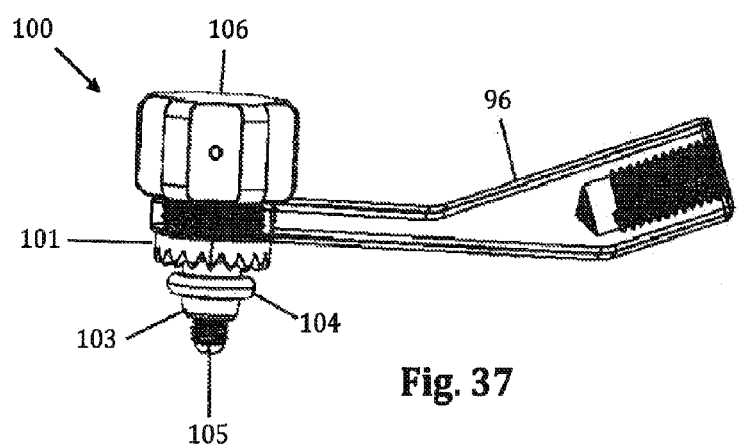

As mentioned above, nerve monitoring may be utilized during advancement and retraction of the retraction assembly 10. According to one example, as pictured in FIG. 29, the nerve monitoring component of the retractor system is the center retractor blade 12, which may be made of a conductive material (e.g. aluminum) and coated with a insulative coating to direct stimulation from the nerve monitoring system to the tissue adjacent the distal end. To direct stimulation to the posterior blade 12, a stimulation clip 550 of the nerve monitoring system may be connected to the set screw 13 used to couple the posterior blade 12 to the translating arm 17. When a stimulation signal is emitted from the stimulation clip 550 it will travel through the set screw 13 and into the blade through an uninsulated contact region with the blade. In order to reduce shunting of current between the set screw and retractor body 20 a special set screw 760 which is configured to reduce shunting of electrical current through the retractor body, as illustrated in FIGS. 31A and 31B. The setscrew 760 has a composite (e.g. PEEK) contact surface 762 where the setscrew 760 engages the retractor body, and a metal contact surface 764 where the setscrew 760 engages the stimulation clip 550. This isolates the electrical current delivered to the center blade 12 through a stimulation clip 550 to the retractor blade 12 and prevents shunting of the current through the retractor body. As described above, the blade is generally insulated based on the anodized aluminum construction. The retractor body which has a DSC coating is not insulated. Thus the center blade 12 itself insulates the current from the retractor body at all points of contact except the setscrew 760. The peek component 762 at the bottom of the setscrew 760 accomplishes this.

According to another example embodiment, pictured in FIGS. 40-48 the nerve monitoring components of the tissue retraction assembly includes 2 main components: a disposable electrode 450 and a center (posterior) blade 500, that replaces the center blade 12, designed to couple to the disposable electrode 450. A stimulation clip 550 may be used to connect the disposable electrode to the nerve monitoring system. One potential advantage of the disposable electrode and accompanying center blade is the increased ability to attain consistent and repeatable nerve monitoring functionality throughout the course of a single surgery and from surgery to surgery (since there is no risk of erosion of the insulative coating on the blade which can lead to current shunting). Two potential barriers to achieving this consistent and repeatable functionality are current shunting and reductions in current density at the distal end of an electrode which can potentially affect the sensitivity of nerve monitoring equipment as a result of conductive metallic devices in the immediate vicinity of the distal tip of the stimulating electrodes. To combat this potential, a locking intradiscal shim (similar to the shims in FIGS. 11-13) with an insulative coating has been developed as a novel solution. By way of the example the insulative coating may be a parylene coating.

FIGS. 40-48 illustrate an example of one embodiment of the removably couplable disposable electrode 450 and retractor blade 500 for use with the tissue retraction assembly 10 according to the present invention. The disposable electrode 450 assists in the detection of nerves during insertion and positioning of the tissue retraction assembly within the operative corridor and surgical target site, as described above (similar to the electrodes 23). Using a disposable electrode permits the retractor blade 500 to be sterilized and reused endlessly without the possibility of degradation to the electrode. This in turn ensures that results from nerve monitoring using the electrode are consistent and reduces potentially high costs of replacing the entire blade structure if the electrode (or insulating regions surrounding the electrode) degrade.

Figure 40:
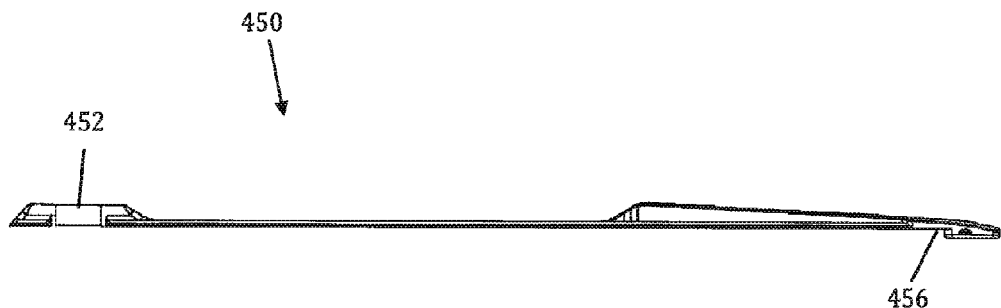
FIGS. 40-41 are side and perspective views, respectively, of an example of a disposable electrode forming part of the tissue retraction system of FIG. 1 according to one embodiment of the present invention.
Figure 41:
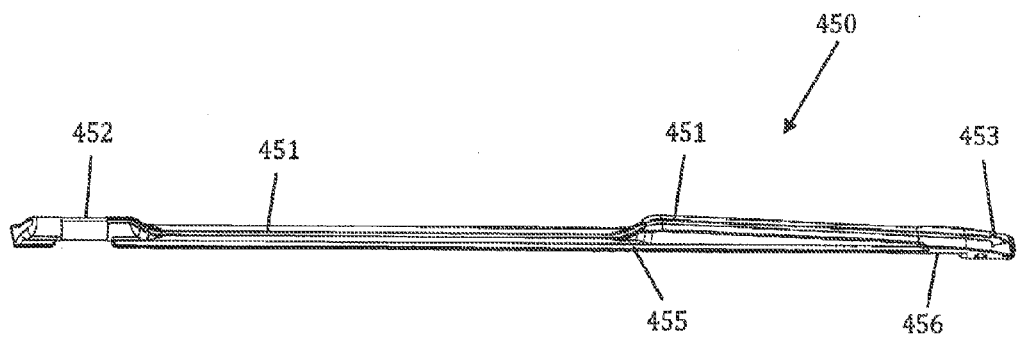
Figure 42:
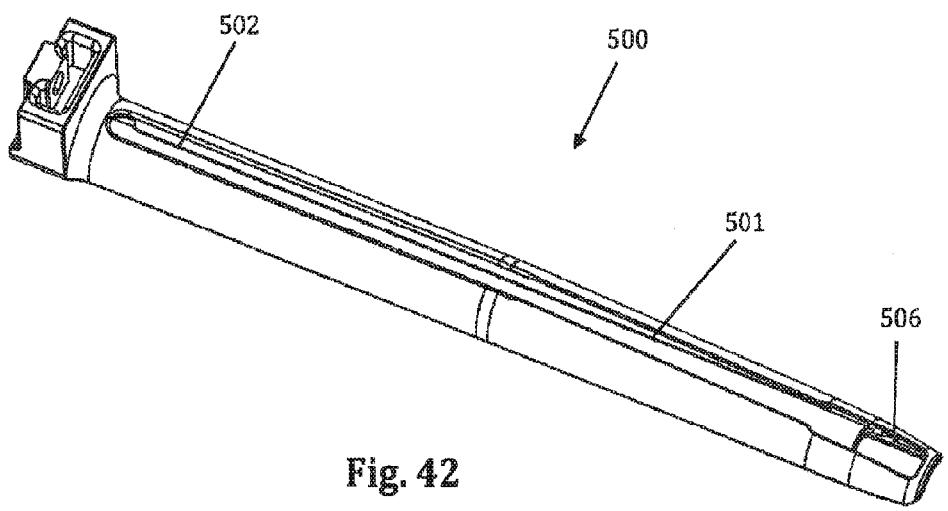
FIGS. 42-43 are perspective views of an example of a retractor blade forming part of the tissue retraction system of FIG. 1 configured to releasably couple with the disposable electrode of FIG. 41.
Figure 43:
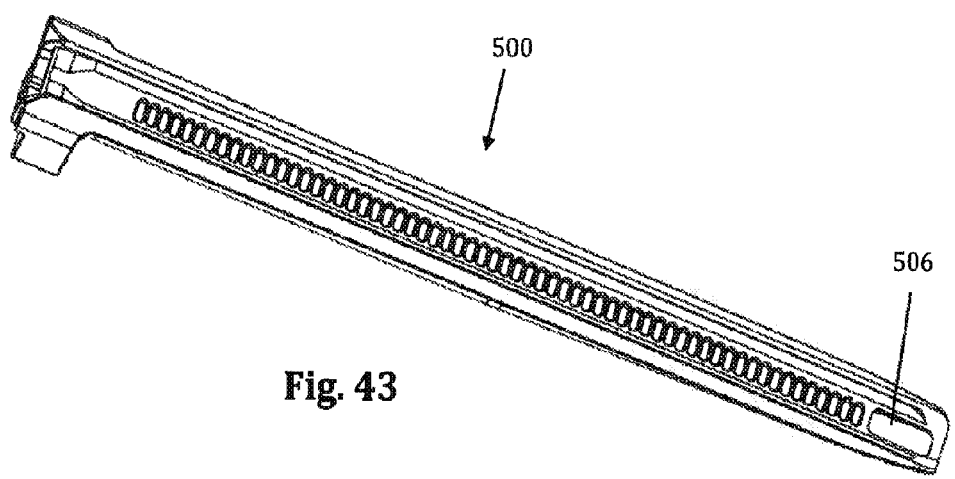
Figure 44:
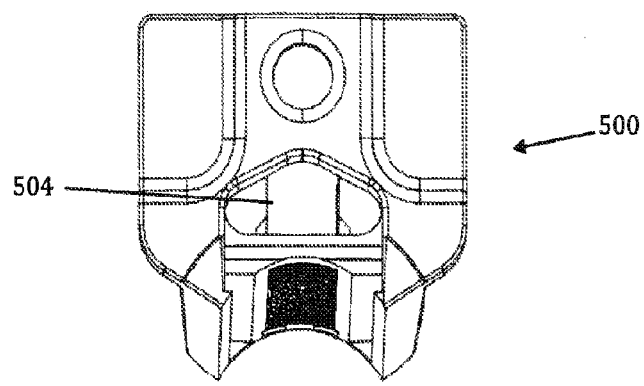
FIG. 44 is top perspective view of the retractor blade of FIG. 42.

FIGS. 40-41 illustrate one example of a disposable electrode 450 that includes a molded plastic part with a conductive trace 451 deposited generally along the length of the disposable electrode 450. Preferably, the disposable electrode 450 is made out of a generally stiff material that can also withstand bending without breaking, such as, for example, PVC. The conductive trace 451 provides a conductive pathway for the delivery of current from a current delivery source (such as a stimulation clip 550) to the distal end of the disposable electrode 450. There are generally two areas along the disposable electrode where the conductive trace 451 is exposed for enabling the delivery of current to and from the disposable electrode 450. By way of example, the proximal end of the disposable electrode 450 has a first exposed area 452 which allows a current delivery source to deliver an electric current to the conductive trace 451. The first exposed area 452 may wrap around the circumference of the proximal end of the disposable electrode 450 to ensure a conductive path between the disposable electrode 450 and a current delivery device (such as, for example, a stimulation clip 550). The distal end of the disposable electrode 450 has a second exposed area 453 (shown by way of example as a triangular patch) for emission of the electric current from the distal end of the disposable electrode 450. Other than the exposed areas 452, 453, the remainder of the conductive trace 451 is insulated with a dielectric coating to prevent current shunting. Any number of conductive materials suitable for completing the current pathway, such as, for example, silver, or copper may be used in the conductive trace 451 without departing from the scope of the present invention.

Figure 47:
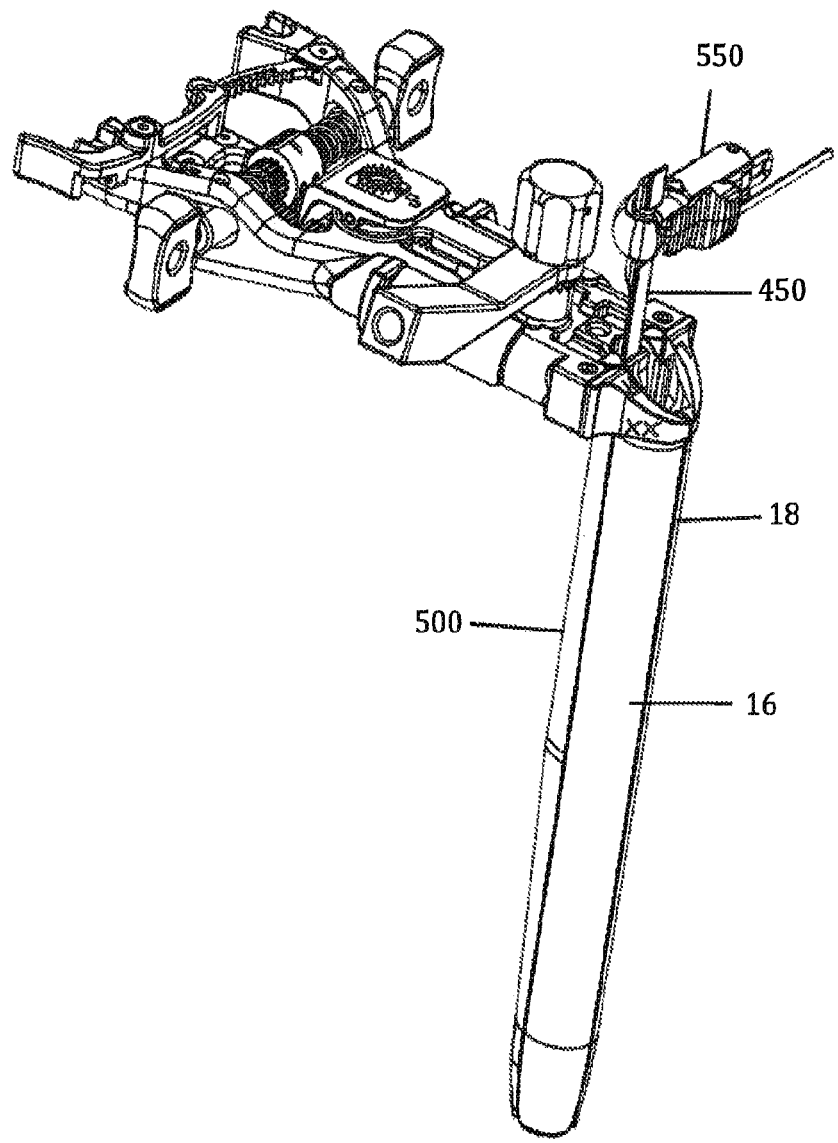
FIGS. 47-48 are perspective views of the tissue retraction assembly of FIG. 2 including the disposable electrode/blade assembly of FIG. 45.
Figure 48:
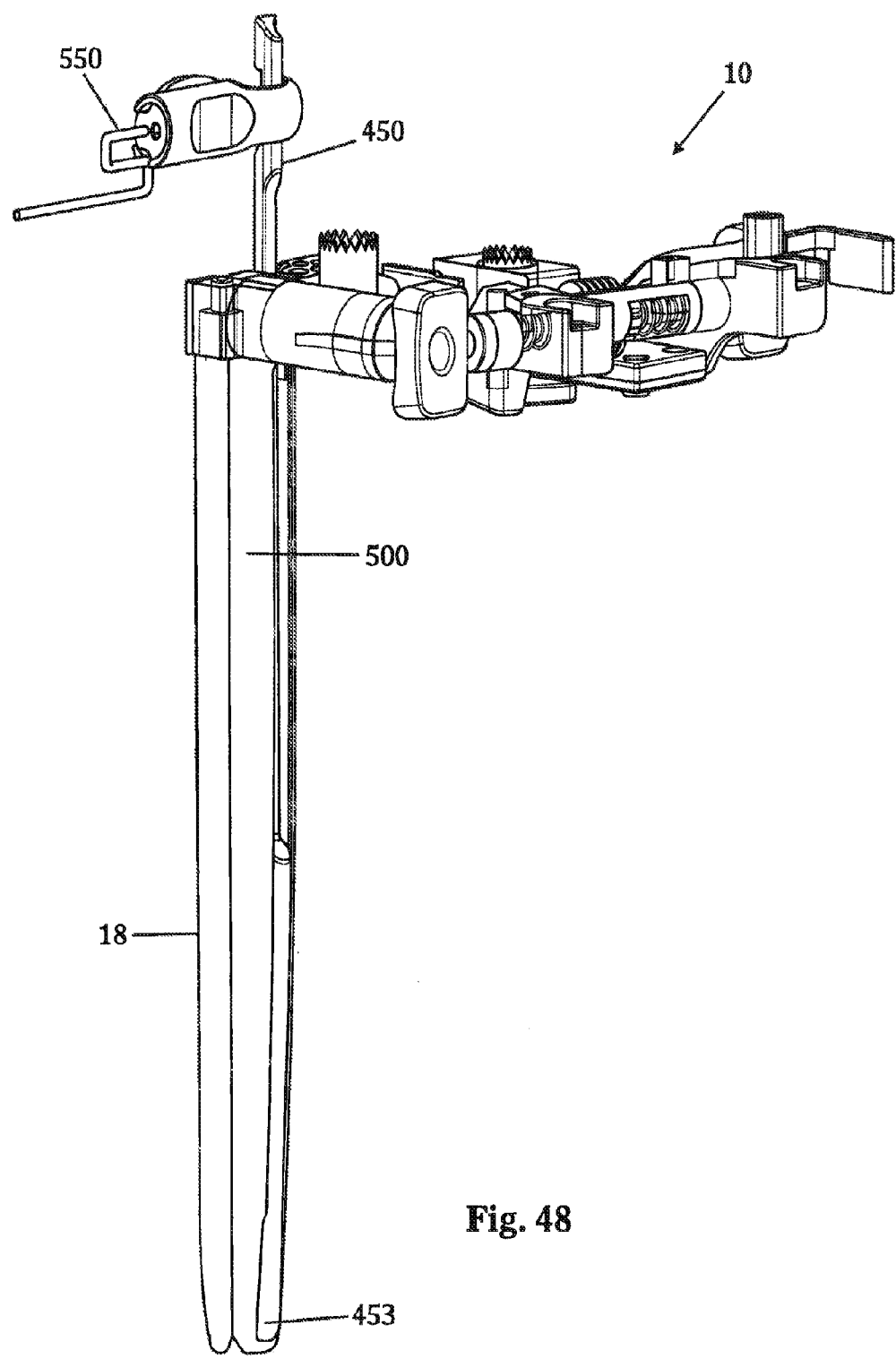

The first exposed area 452 of the disposable electrode may have a generally cylindrical shape for facilitating the connection between the electrode and a nerve monitoring system. For example, as shown in FIGS. 47-48, an electrical coupler is shown in the form of a plunger clip. Although shown as cylindrical, the connection site for a current delivery device may be any size and shape necessary for making a quality electrical connection without departing from the scope of the present invention. The remainder of the body of the disposable electrode 450 may be generally flat with minimal thickness and a variety of features for engaging and securing the disposable electrode 450 to a retractor blade 500. For example, wings 455 may extend from the sides of the disposable electrode 450 for engaging positioning features within the retractor blade 500, as will be discussed in more detail below. Additionally, the distal end of the disposable electrode 450 may have a ledge 456 for engaging a feature of the retractor blade 500 for further secure positioning of the disposable electrode 450 relative to the retractor blade 500, as will also be discussed in more detail below. A single sized disposable electrode 450 is designed to be used with a variety of retractor blade 500 sizes and shapes (for example, retractor blade lengths generally ranging from 20 to 180 mm), but the disposable electrodes may also be available in a variety of shapes and sizes.

Figure 45:
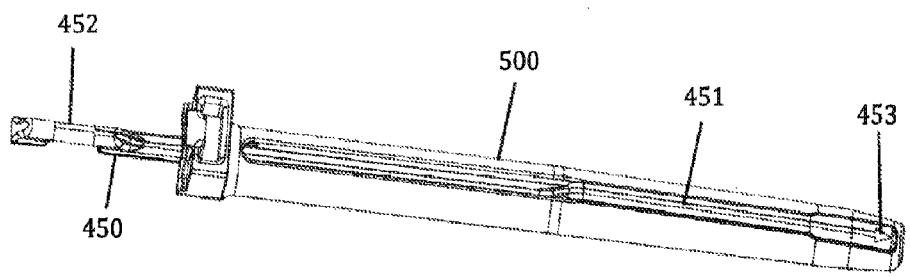
FIGS. 45-46 are perspective views of an assembly comprising the disposable electrode of FIG. 40 coupled to the retractor blade of FIG. 42.
Figure 46:
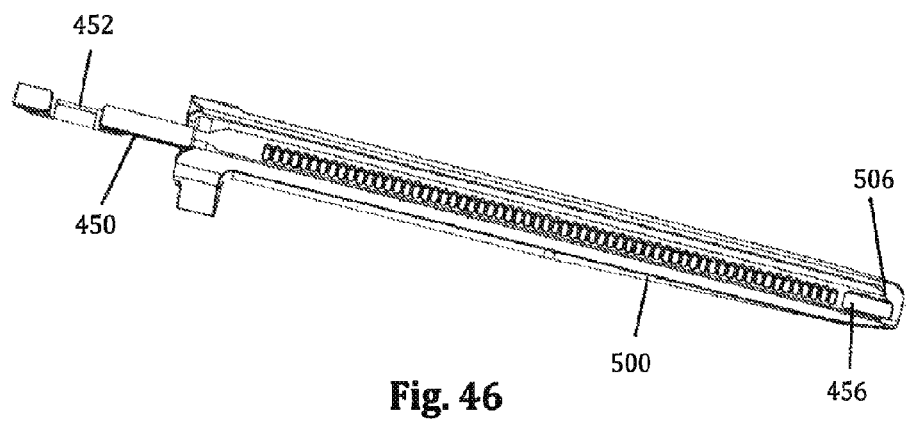

FIGS. 45-46 illustrate one example assembly of a disposable electrode 450 releasably coupled to retractor blade 500. Preferably, at least the posterior blade is configured to enable the coupling of a disposable electrode 450. During assembly of the disposable electrode 450 to the retractor blade 500, the proximal end of the disposable electrode 450 (more specifically, adjacent the first exposed area 452 end of the disposable electrode 450) is inserted into generally the distal end of the retractor blade 500. The wings 455 of the disposable electrode 450 mate with and are constrained by the dovetail grooves 502 which extend longitudinally from the distal end to the proximal end of the retractor blade 500. The dovetail grooves 502 provide an insertion guide for the disposable electrode 450 as it is inserted and assists in maintaining proper positioning of the disposable electrode 450 while coupled to the retractor blade 500. Additionally, the ledge 456 near the distal end of the disposable electrode 450 may engage the cut-out 506 generally near the distal end of the retractor blade 500 to further assist in securing the positioning of the disposable electrode 450 relative to the retractor blade 500. Therefore, the disposable electrode 450 is adapted to the retractor blade 500 so that the second exposed area 453 (shown by way of example as triangular in FIGS. 41 and 45) is exposed generally along the outer surface of the blade (best shown in FIG. 45). Furthermore, the proximal end of the disposable electrode 450 protrudes from a machined cavity 504 (best shown in FIG. 44) at the proximal end of the retractor blade 500. Depending on the height of the blade, the proximal end may be bent or folded so as not to obstruct the surgical corridor. While the disposable electrode 450 and associated retractor blade 500 have been described herein for use with the retractor assembly 10, particularly for lateral access to the lumbar spine, it is contemplated that the disposable electrode retractor blade combination may be useful in a variety of surgical procedures (e.g. in a cervical procedure for stimulating the recurrent laryngeal nerve to monitor status of the nerve during retraction to access the anterior cervical spine). The cut-out 506 may also be useful as an alignment tool to ensure that the retractor assembly is properly aligned. By way of example, it is generally preferable to have the posterior blade aligned perpendicular to the disc space such that the cephalad and caudal blades expand directly anterior. Holes (not show) may be provided at the distal end of each of the cephalad and caudal blades. The holes will be distinguishable when viewed on a fluoroscopy image if they are not obstructed by a radiodense object. When the retractor assembly is properly aligned with the disc space and the retractor blades are in the closed position, the cut-out 506 is visible in a lateral fluoroscopic image and the holes line up with the cut-out 506 and are also visible. If the holes are not visible, the retractor may need to be realigned. According to another example, a second set of alignment holes may be included (either above or below the first set of holes) such that the horizontal alignment of the retractor assembly 10 relative to the spine may also be assessed.

Figure 49:
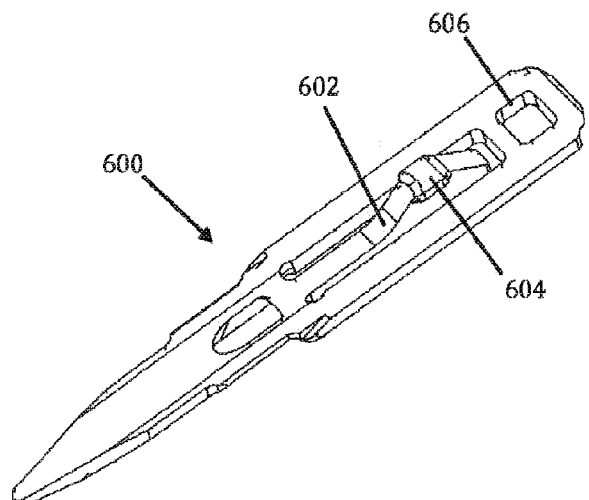
FIGS. 49-51 illustrate an example of an insulated locking shim for use with the center blade forming part of the tissue retraction system of FIG. 2 to prevent current shunting from the center blade when neurophysiologic monitoring is performed from the center blade.
Figure 50:
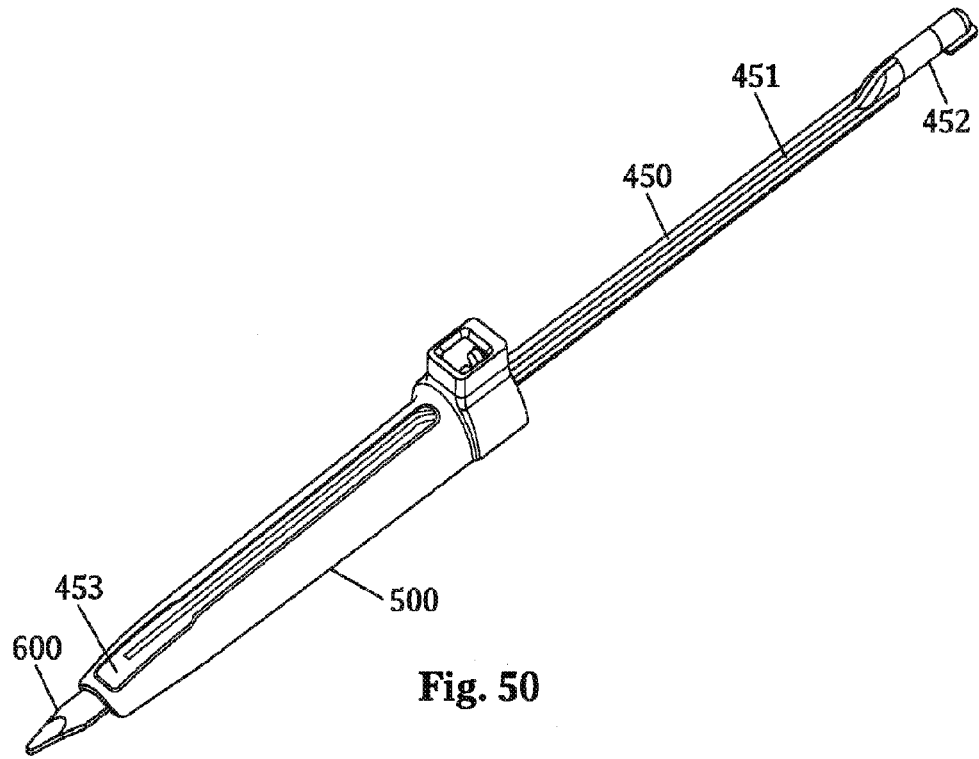
Figure 51:
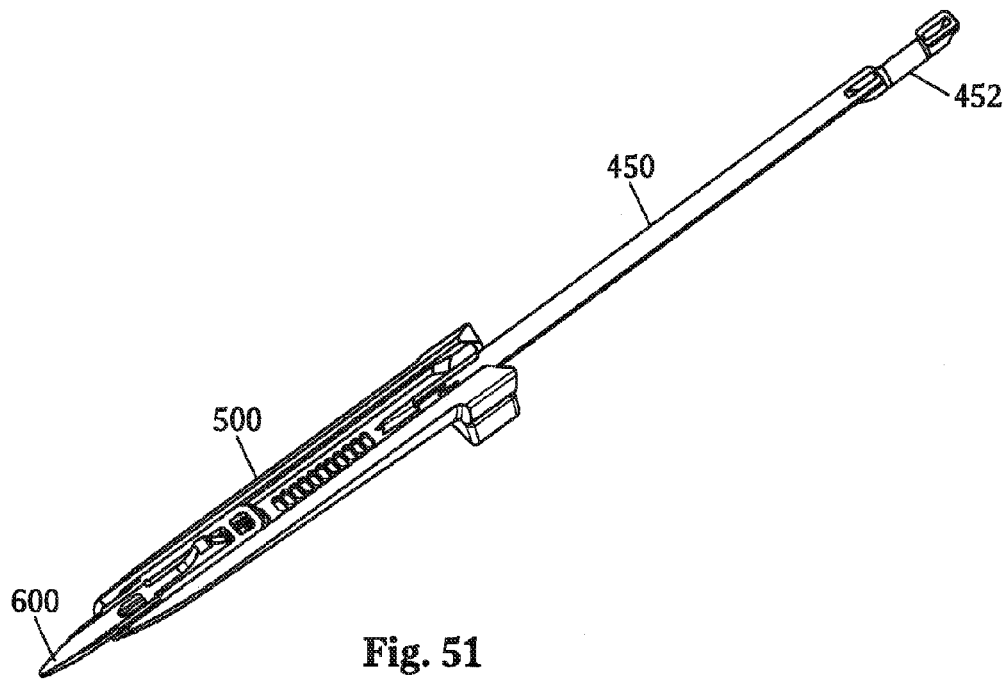
Figure 52:
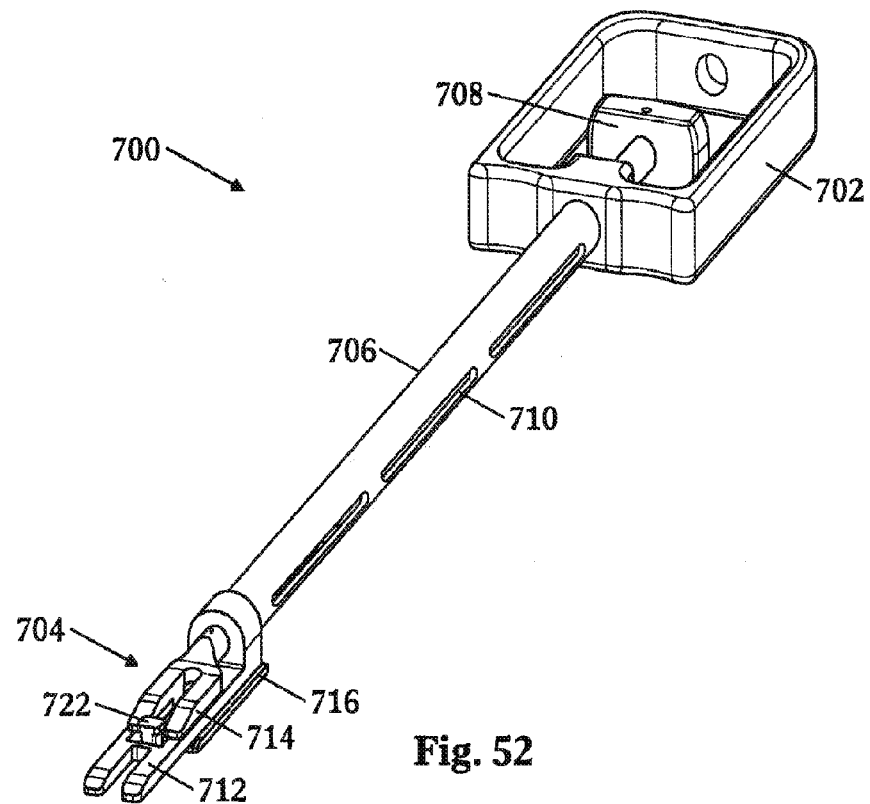

FIG. 49 is illustrates a locking intradiscal shim 600 designed for use with the center blade 500 and disposable electrode 450, according to an example embodiment. The locking intradiscal shim 600 is similar to the shim 25 of FIGS. 10-12 such that a description of all the like elements will not be repeated here. The locking intradiscal shim 600 of FIG. 49 is preferably coated with an insulative parylene coating to mitigate current shunting and changes to current density at the distal tip of the disposable electrode. Parylene is the trade name for a variety of chemical vapor deposited poly (p-xylylene) polymers used as moisture barriers and electrical insulators. Among such polymers, Parylene C is may be particularly suited due to its combination of barrier properties and manufacturing advantages. The locking intradiscal shim 600 includes a deflectable tab 602 with a lip member 604 that serves as a locking feature. The shim 600 further includes a cut-out 606 that receives an engagement tab of a removal tool. FIGS. 50-51 illustrate the locking intradiscal shim of FIG. 49 coupled to and extending from the distal end of the blade 500 with the disposable electrode 450 also coupled to the blade 500.

FIGS. 52-55 illustrate a shim removal tool 700 according to a second example embodiment. By way of example only, the shim removal tool 700 is shown and described herein in conjunction with the locking intradiscal shim 600 of FIGS. 49 and 50, although it is to be readily appreciated that the shim removal tool may be employed in a similar manner with other locking shims according to the present invention.

The shim removable tool 700 includes a proximal grip cage 702, a distal engagment region 704, and an elongated shaft 706 extending therebetween. The proximal grip cage may be generally rectangular in shape and provides a grip for manipulating the tool and also provides a strike surface for impacting the instrument if necessary. The grip cage 702 also surrounds the thumb release 708, which is connected to the distal region 704 via a spring mechanism 710. The distal region 704 includes a shim fork 712 and a release fork 714. The shim fork 712 includes a guide track 716 that engages the track in the retractor blade (described above). The split ramp 718 at the distal end of the shim fork 712 slides along the front of the shim 600 and engages behind the lip member 604, lifting the engagement tab on the back side of the removal lip 604 and disengaging the tab from the track guide. This can be done to remove the shim 600 completely from the blade or to simply reposition the shim higher (or lower) along the length of the blade track. As the split ramp 718 fully seats around the removal lip 604, an engagement tab 720 on the shim fork 712 catches in the cutout 606 in the shim 600, locking the shim fork 712 to the shim 600. The release fork 714 may be engaged to remove the engagement tab 720 of the shim fork 712 from the shim 600. Depressing the thumb release 708 moves the release fork 714 distally where the split ramp 718 of the release fork 714 engages behind the removal lip 722 of the shim fork 712, lifting the engagement tab 720 out of the cutout 606 in the shim 600. At the same time, knobs 724 on the release fork 714 push distally on the shim 600 causing the shim fork 712 to slide proximally and disengage from the removal lip 604 of the shim 600.

FIG. 56 illustrates a shim removal tool 750 according to a third example embodiment. The shim removal tool 750 works like the shim removal tool 700 of FIG. 52 except that it includes only a shim fork 752 and not a release fork. Thus once the shim fork 752 is engaged the shim must be removed from the blade track before the tool can be disengaged. The shim fork 750 works as described with regard to the removal tool 700. The removal tool 750 includes a strike plate 754 for delivering an impaction force to the removal tool. The strike plate 754 includes a threaded hole for connecting additional instruments such as a slap hammer (to aid removal of the shim).

As mentioned above, the dilation assembly 7 and retraction assembly 10 of the surgical access system 6 may be configured to detect the presence of (and optionally the distance and/or direction to) neural structures during tissue dilation and/or retraction. This is accomplished by employing the following steps: (1) one or more stimulation electrodes are provided on the various dilation and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist). Such monitoring may also be carried out via the surgeon-driven EMG monitoring system shown and described in the '949 and '840 patents referenced above, as well as PCT Applications PCT/US02/30617 and PCT/US2008/004427, both of which are incorporated herein by reference as if set forth entirely herein. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 57:
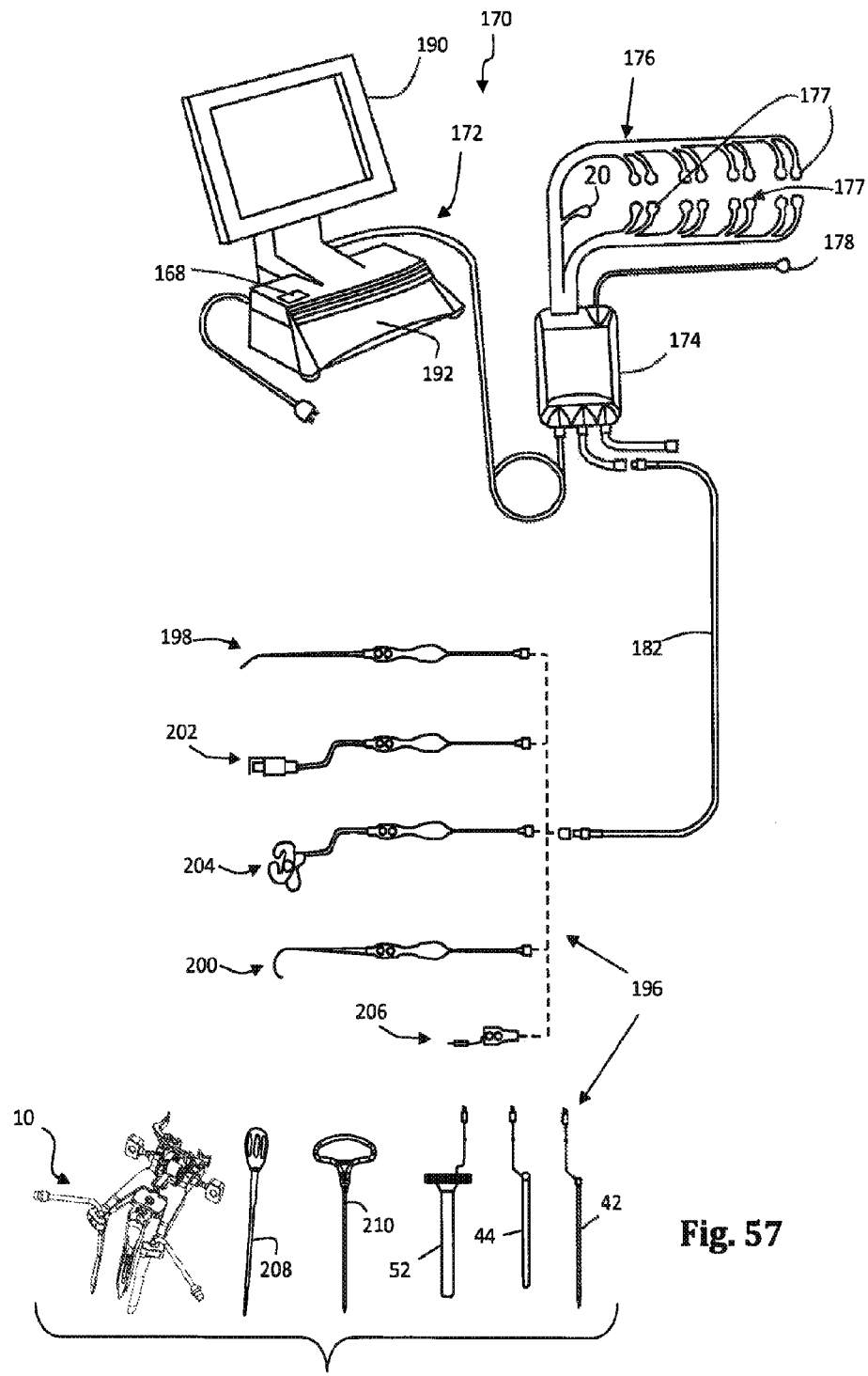
FIG. 57 is a perspective view of an example of a nerve monitoring system programmed to perform nerve monitoring before, during and after the creation of an operative corridor to a surgical target site using the surgical access system of FIG. 2 in accordance with the present invention.
Figure 58:
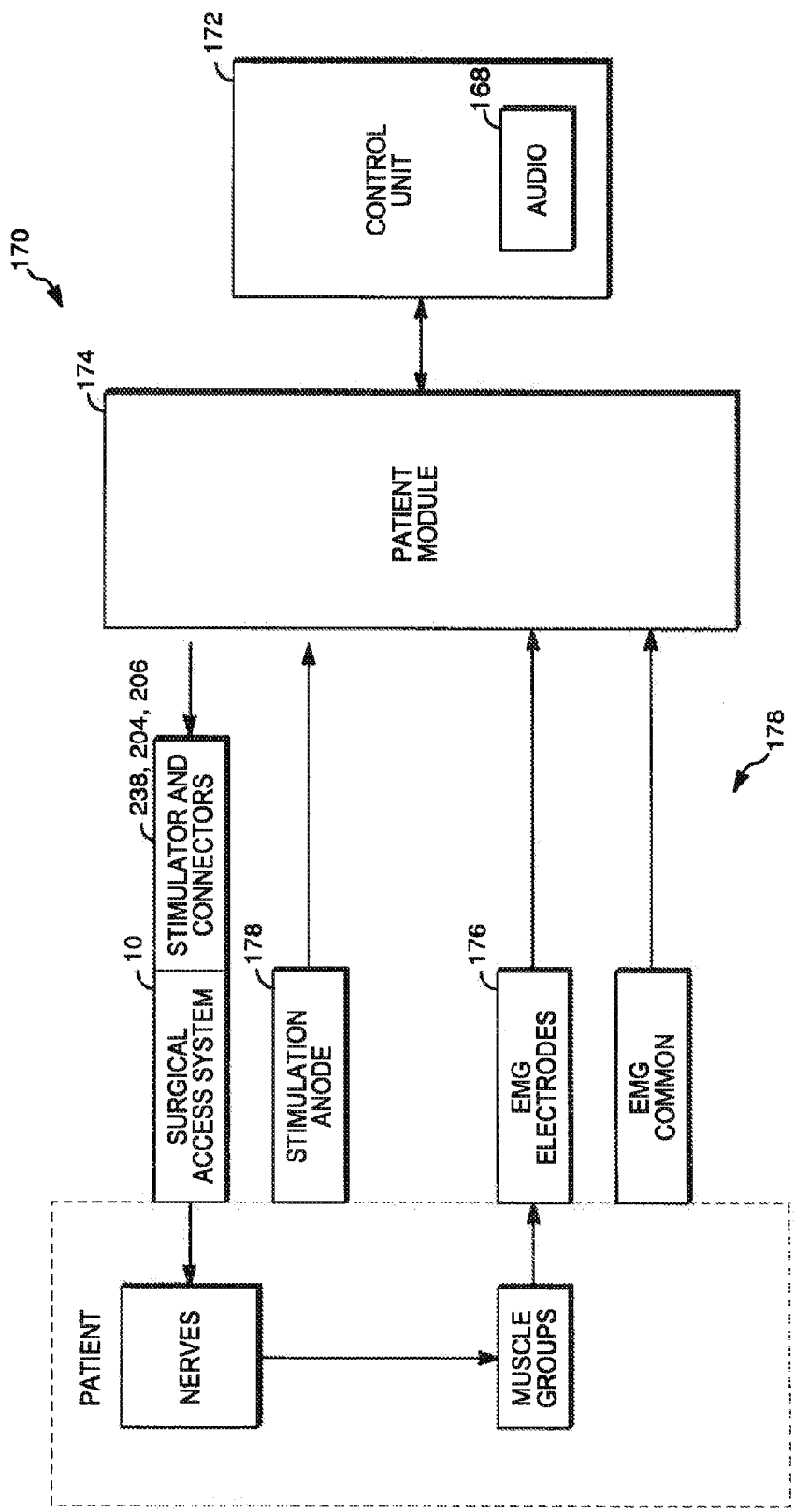
FIG. 58 is a block diagram of the nerve monitoring system shown in FIG. 57.

FIGS. 57-58 illustrate one such monitoring system 170, by way of example only, suitable for use with the surgical access system 6 of the present invention. The monitoring system 170 includes a control unit 172, a patient module 174, and an EMG harness 176 and return electrode 178 coupled to the patient module 174, and a cable 182 for establishing electrical communication between the patient module 174 and any number of surgical accessories 196, including the surgical access system of the present invention (retractor assembly 10 of FIG. 2, dilators 8 and 9 of FIG. 1, K-wire 42 of FIG. 57). The surgical accessories 196 may further include, but are not necessarily limited to, devices for performing pedicle screw tests (such as a screw test probe 198), neural pathology monitoring devices (such as a nerve root retractor 200), coupling devices for electronically coupling surgical instruments to the system 170 (such as electric coupling devices 202, 204 and stimulator driver 206), and pilot hole forming components (such as a tap member 208, pedicle access probe 210, or other similar device). More specifically, this electrical communication can be achieved by providing, by way of example only, a hand-held stimulation driver 206 capable of selectively providing a stimulation signal (due to the operation of manually operated buttons on the hand-held stimulation controller 206) to one or more connectors (e.g., coupling devices 202, 204). The coupling devices 202, 204 are suitable to establish electrical communication between the hand-held stimulation controller 206 and (by way of example only) the stimulation electrodes on the K-wire 42, the dilators 8 and 9, the retractor blades 12, 16, 18, and/or the shim members 22, 25 (collectively "surgical access instruments").

In order to use the monitoring system 170, then, these surgical access instruments must be connected to at least one of coupling devices 202, 204 (or their equivalent), at which point the user may selectively initiate a stimulation signal (preferably, a current signal) from the control unit 172 to a particular surgical access instruments. Stimulating the electrode(s) on these surgical access instruments before, during, and/or after establishing operative corridor will cause nerves that come into close or relative proximity to the surgical access instruments to depolarize, producing a response in a myotome associated with the innervated nerve.

The control unit 172 includes a touch screen display 190 and a base 192, which collectively contain the essential processing capabilities (software and/or hardware) for controlling the monitoring system 170. The control unit 172 may include an audio unit 168 that emits sounds according to a location of a surgical element with respect to a nerve. The patient module 174 is connected to the control unit 172 via a data cable 194, which establishes the electrical connections and communications (digital and/or analog) between the control unit 172 and patient module 174. The main functions of the control unit 172 include receiving user commands via the touch screen display 190, activating stimulation electrodes on the surgical access instruments, processing signal data according to defined algorithms, displaying received parameters and processed data, and monitoring system status and report fault conditions. The touch screen display 190 is preferably equipped with a graphical user interface (GUI) capable of communicating information to the user and receiving instructions from the user. The display 190 and/or base 192 may contain patient module interface circuitry (hardware and/or software) that commands the stimulation sources, receives digitized signals and other information from the patient module 174, processes the EMG responses to extract characteristic information for each muscle group, and displays the processed data to the operator via the display 190.

In one embodiment, the monitoring system 170 is capable of determining nerve direction relative to one or more of the K-wire 42, the dilators 8 and 9, the retractor blades 12, 16, 18, and/or the shim elements 22, 25 before, during and/or following the creation of an operative corridor to a surgical target site. Monitoring system 170 accomplishes this by having the control unit 172 and patient module 174 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 176. The nerve direction feature of the system 170 is based on assessing the evoked response of the various muscle myotomes monitored by the system 170 via the EMG harness 176.

By monitoring the myotomes associated with the nerves (via the EMG harness 176 and recording electrode 177) and assessing the resulting EMG responses (via the control unit 172), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 6 after the operative corridor has been established. In spinal surgery, for example, this is particularly advantageous in that the surgical access system 6 may be particularly suited for establishing an operative corridor to an intervertebral target site in a postero-lateral, trans-psoas fashion so as to avoid the bony posterior elements of the spinal column.

Figure 59:
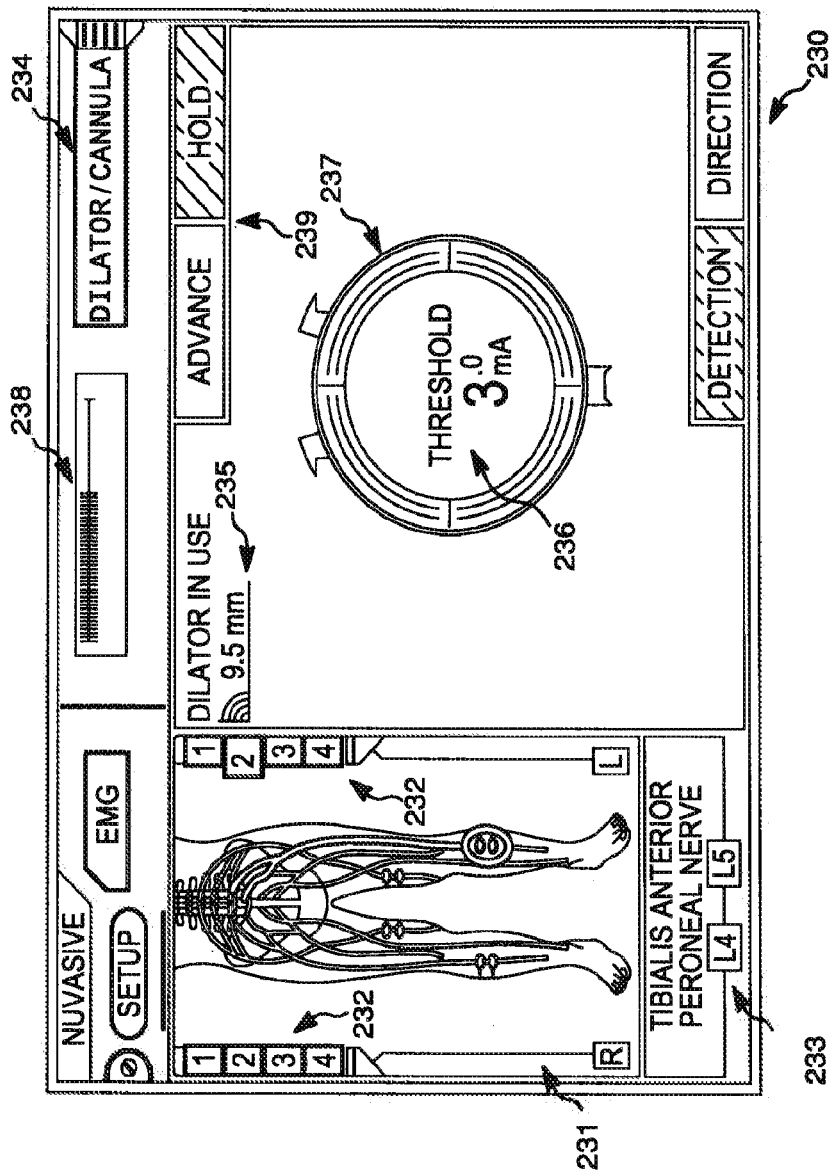
FIGS. 59-60 are examples of screen displays illustrating exemplary features and information communicated to a user during the use of the nerve monitoring system of FIG. 57.
Figure 60:
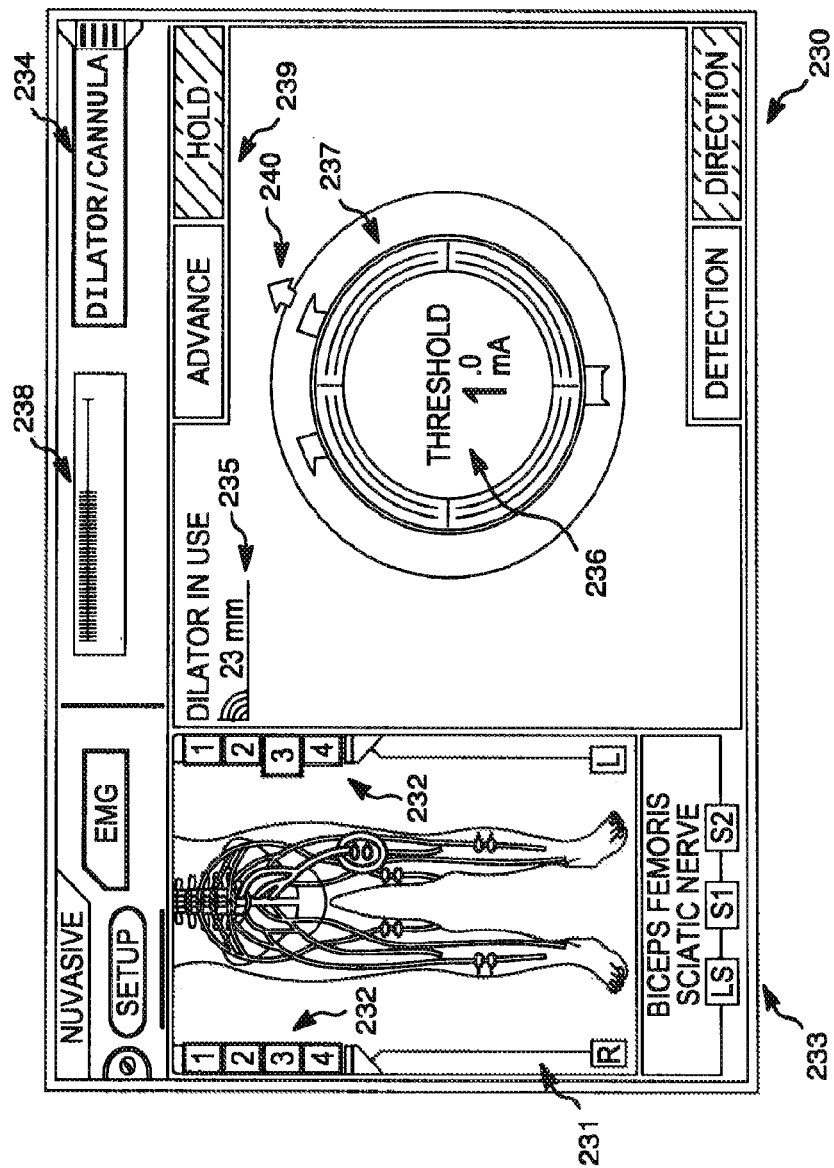

FIGS. 59-60 are exemplary screen displays (to be shown on the display 190) illustrating one embodiment of the nerve direction feature of the monitoring system shown and described with reference to FIG. 57-58. These screen displays are intended to communicate a variety of information to the surgeon in an easy-to-interpret fashion. This information may include, but is not necessarily limited to, a display of the function 230 (in this case "DIRECTION"), a graphical representation of a patient 231, the myotome levels being monitored 232, the nerve or group associated with a displayed myotome 233, the name of the instrument being used 234 (in this case, a dilator), the size of the instrument being used 235, the stimulation threshold current 236, a graphical representation of the instrument being used 237 (in this case, a cross-sectional view of a dilator 8 or 9) to provide a reference point from which to illustrate relative direction of the instrument to the nerve, the stimulation current being applied to the stimulation electrodes 238, instructions for the user 239 (in this case, "ADVANCE" and/or "HOLD"), and an arrow 240 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 234), it is to be readily appreciated that the present invention is deemed to include providing similar information on the display 190 during the use of any or all of the various instruments forming the surgical access system 6 of the present invention, including the dilation assembly 7 (i.e. the K-wire 42 and dilators 8 and 9) and/or the retractor blade 12 or the shim elements 22, 25.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction and/or removal of bone products (such as allograft or autograft) and/or devices having ceramic, metal and/or plastic construction (such as mesh) and/or compounds such as bone morphogenic protein), total disc replacement, etc.

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

We claim:

1. A retractor assembly for creating an operative corridor to a spinal surgical target site, comprising:
    a retractor body and a plurality retractor blades extending generally perpendicularly to the retractor body, the retractor body being operable to separate the plurality of retractor blades relative to each to other to retract tissue away from an interior of the retractor blades when the tissue retractor assembly is advanced to the surgical target site and the retractor blades are separated to thereby form an operative corridor to the surgical target site; and
    a supplemental retractor blade assembly attachable to two of the plurality of retractor blades, the supplemental retractor blade assembly comprising an elongated supplemental retractor blade and a crossbar connector, the crossbar connector extending from a first end to a second end and including an elongated slot, the elongated slot opening in the first end and configured to engage a post extending perpendicularly from each of the two retractor blades.

2. The retractor assembly of claim 1, wherein said post is on each of said two retractor blades, the posts being configured to be received in the elongated slot through the opening in the first end, the posts further including enlarged ends that are larger than a height of the slot to prevent disengagement of the crossbar connector from the two blades.

3. The retractor assembly of claim 2, wherein the posts of the two retractor blades can slide along the elongated slot while the supplemental retractor blade is maintained in a fixed position in order to permit opening or closing of the two retractor blades.

4. The retractor assembly of claim 2, wherein the crossbar connector includes a rear face configured to interlock with a series of grooves on the supplemental retractor blade to maintain a desired depth of the supplemental retractor blade relative to the crossbar connector.

5. The retractor assembly of claim 1, wherein the supplemental retractor blade includes a handle attached thereto.

6. The retractor assembly of claim 1, wherein the plurality of retractor blades includes at least three retractor blades, the at least three retractor blades comprising a caudal blade, a cephalad blade, and a center blade, and wherein the crossbar connector engages the caudal blade and the cephalad blade.

7. The retractor assembly of claim 1, wherein the crossbar connector elongate slot slidably receives the post of each of the two retractor blades to attach the crossbar connector to the two retractor blades of the retractor assembly.

8. The retractor assembly of claim 7, wherein the crossbar connector further including a rear face configured to engage the supplemental retractor blade.

9. A system for creating an operative corridor to a spinal surgical target site, comprising:
a retractor assembly including a retractor body and a plurality retractor blades extending generally perpendicularly to the retractor body, the retractor body being operable to separate the plurality of retractor blades relative to each other to retract tissue away from an interior of the retractor blades when the tissue retractor assembly is advanced to the surgical target site and the retractor blades are separated to thereby form an operative corridor to the surgical target site, wherein at least one of the plurality of blades is an electrode blade configured to couple to an electrode member, the electrode blade having an interior surface that faces towards the operative corridor and an exterior surface, a distal end with a distal end surface, and a proximal end, the electrode blade having an elongate slot extending longitudinally through the electrode blade and opening along the exterior surface; and
an electrode member removably couplable with said electrode blade and configured to transmit an electrical stimulation signal to tissue adjacent the distal end of the electrode blade, the electrode member configured to be slideably received along the elongate slot.

10. The system of claim 9, wherein the electrode member comprises a nonconductive material having a conductive trace extending the length thereof between a proximal exposed area and a distal exposed area.

11. The system of claim 10, wherein the proximal exposed area is configured to be in electrical communication with a nerve monitoring system.

12. The system of claim 10, wherein the conductive trace is insulated with a dielectric coating to prevent current shunting along its length between the proximal and distal exposed areas.

13. The system of claim 10, wherein the electrode blade further comprises an aperture connecting to the elongate slot adjacent the distal end of the electrode blade.

14. The system of claim 13, wherein the distal exposed area of the elongate electrode is configured to align with the aperture of the electrode blade.

15. A retractor assembly for creating an operative corridor to a spinal surgical target site, comprising:
a retractor body and a plurality retractor blades extending generally perpendicularly to the retractor body, the retractor body being operable to separate the plurality of retractor blades relative to each other to retract tissue away from an interior of the retractor blades when the retractor assembly is advanced to the surgical target site and the retractor blades are separated to thereby form an operative corridor to the surgical target site, the retractor body also being operable to splay at least one of the plurality of retractor blades such that a distal end of the retractor blade extends wider than a proximal end of the retractor blade, wherein splaying of the at least one retractor blade is controlled by a rack and pinion gear situated in the retractor body driven by a lead screw.

16. The retractor assembly of claim 15, wherein the gear provides for continuous splay.

17. The retractor assembly of claim 15, wherein the retractor assembly includes three blades and two of the three retractor blades are splayable.

18. The retractor assembly of claim 17, wherein each of the two splayable retractor blades are independently controlled by a dedicated gear mechanism.

19. The retractor assembly of claim 18, wherein each of the independently controllable gear mechanisms provide for continuous splay.

20. The retractor assembly of claim 19, wherein each of the independently controllable gear mechanisms is a rack and pinion gear driven by a lead screw.

* * * * *